US006923835B2

(12) United States Patent
Sabelle et al.

(10) Patent No.: US 6,923,835 B2
(45) Date of Patent: Aug. 2, 2005

(54) BIS-PARA-PHENYLENEDIAMINE DERIVATIVES COMPRISING A PYRROLIDYL GROUP AND USE OF THESE DERIVATIVES FOR DYEING KERATIN FIBRES

(75) Inventors: Stéphane Sabelle, Paris (FR); Laure Ramos, Bourg Lareine (FR); Madeleine Leduc, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/657,245

(22) Filed: Sep. 9, 2003

(65) Prior Publication Data

US 2004/0123401 A1 Jul. 1, 2004

Related U.S. Application Data

(60) Provisional application No. 60/431,713, filed on Dec. 9, 2002.

(30) Foreign Application Priority Data

Sep. 9, 2002  (FR) ............................................ 02 11133

(51) Int. Cl.$^7$ ................................................ A61K 7/13
(52) U.S. Cl. ........................ 8/409; 8/408; 8/410; 8/411; 8/423; 8/574; 548/541; 548/556; 548/566; 548/570; 548/577; 548/578
(58) Field of Search .......................... 8/409, 408, 410, 8/411, 423, 574; 548/541, 556, 566, 570, 577, 579

(56) References Cited

U.S. PATENT DOCUMENTS

| | | | |
|---|---|---|---|
| 2,261,002 A | 10/1941 | Ritter | 288/570 |
| 2,271,378 A | 1/1942 | Searle | 167/22 |
| 2,273,780 A | 2/1942 | Dittmar | 260/28 |
| 2,375,853 A | 5/1945 | Kirby et al. | 280/588 |
| 2,388,614 A | 11/1945 | Kirby et al. | 167/22 |
| 2,454,547 A | 11/1948 | Bock et al. | 260/567.8 |
| 3,061,432 A | 10/1962 | Menzel et al. | 96/99 |
| 3,206,462 A | 9/1965 | McCarty | 260/256.4 |
| 3,227,554 A | 1/1966 | Barr et al. | 96/55 |
| 3,419,391 A | 12/1968 | Young | 96/56.5 |
| 3,725,067 A | 4/1973 | Bailey et al. | 96/56.5 |
| 3,758,309 A | 9/1973 | Bailey et al. | 96/136 |
| 3,874,870 A | 4/1975 | Green et al. | 71/107 |
| 3,915,921 A | 10/1975 | Schlatzer, Jr. | 260/17.4 |
| 3,926,631 A | 12/1975 | Arai et al. | 96/29 |
| 3,929,990 A | 12/1975 | Green et al. | 474/78 |
| 3,966,904 A | 6/1976 | Green et al. | 424/78 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/329 |
| 4,026,945 A | 5/1977 | Green et al. | 260/567.6 |
| 4,027,020 A | 5/1977 | Green et al. | 424/248.56 |
| 4,128,425 A | 12/1978 | Greenwald | 96/66 |

(Continued)

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 42 34 886 A1 | 4/1994 |
| DE | 42 41 532 | 6/1994 |
| DE | 195 43 988 | 5/1997 |
| DE | 299 01 593 | 4/1999 |
| DE | 299 02 262 | 5/1999 |
| DE | 100 34 617 A1 | 1/2002 |
| EP | 0 119 860 | 9/1984 |
| EP | 0 122 324 | 10/1984 |
| EP | 0 173 109 | 3/1986 |
| EP | 0 216 479 | 4/1987 |
| EP | 0 244 160 | 11/1987 |
| EP | 0 285 274 | 10/1988 |
| EP | 0 304 001 | 2/1989 |
| EP | 0 456 226 | 11/1991 |
| EP | 0 488 248 | 6/1992 |
| EP | 0 488 909 | 6/1992 |
| EP | 0 518 238 | 12/1992 |
| EP | 0 557 851 | 9/1993 |
| EP | 0 578 248 | 1/1994 |
| EP | 0 714 954 | 6/1996 |
| EP | 0 770 375 | 5/1997 |
| EP | 0 943 614 A2 | 9/1999 |
| EP | 0 962 452 | 12/1999 |
| EP | 1 018 508 A1 | 7/2000 |
| FR | 1 400 366 | 4/1965 |
| FR | 2 075 583 | 10/1971 |

(Continued)

OTHER PUBLICATIONS

Co–pending U.S. Appl. No. 09/959,913, filed Mar. 31, 2001.
Co–pending U.S. Appl. No. 10/397,245, filed Mar. 27, 2003.
Co–pending U.S. Appl. No. 10/433,408, filed Jun. 4, 2003.
Co–pending U.S. Appl. No. 10/433,411, filed Oct. 29, 2003.
Co–pending U.S. Appl. No. 10/433,687, filed Jun. 5, 2003.
Co–pending U.S. Appl. No. 10/433,688, filed Nov. 5, 2003.
Co–pending U.S. Appl. No. 10/433,689, filed Nov. 12, 2000.
Co–pending U.S. Appl. No. 10/603,831, filed Jun. 26, 2003.
Co–pending U.S. Appl. No. 10/612,986, filed Jul. 7, 2003.
E. Hannig et al., "Kurze Orginalmitteilungen", Die Pharmazie, p. 231, 1980.
E.J. Browne et al., "Triazoles. Part VII.* Syntheses of Substituted 1,2,4–Triazoles", Journal of The Chemical Society, pp. 5149–5152, 1962.

(Continued)

*Primary Examiner*—Margaret Kinsmann
*Assistant Examiner*—Eisa Elhilo
(74) *Attorney, Agent, or Firm*—Finnegan, Henderson, Farabow, Garrett & Dunner, L.L.P.

(57) ABSTRACT

The invention relates to novel bis-para-phenylenediamine derivatives containing a pyrrolidyl group substituted with a cationic radical, to dye compositions containing them and to the process of dyeing keratin fibres using these compositions.

The present invention makes it possible to obtain a chromatic, powerful, sparingly selective and colourfast coloration of keratin fibres.

34 Claims, No Drawings

U.S. PATENT DOCUMENTS

| | | | | |
|---|---|---|---|---|
| 4,157,388 A | 6/1979 | Christiansen | ................. | 424/70 |
| 4,349,532 A | 9/1982 | Vanlerberghe et al. | ......... | 424/47 |
| 4,390,689 A | 6/1983 | Jacquet et al. | .............. | 528/335 |
| 4,500,548 A | 2/1985 | Silva | ............................ | 426/19 |
| 4,500,630 A | 2/1985 | Sato et al. | ................... | 430/386 |
| 4,509,949 A | 4/1985 | Huang et al. | ................ | 586/558 |
| 4,540,654 A | 9/1985 | Sato et al. | ................... | 430/381 |
| 4,608,250 A | 8/1986 | Jacquet et al. | ................. | 424/71 |
| 4,621,046 A | 11/1986 | Sato et al. | ................... | 430/381 |
| 4,702,906 A | 10/1987 | Jacquet et al. | ................. | 424/70 |
| 4,719,282 A | 1/1988 | Nadolsky et al. | ............ | 528/310 |
| 4,823,985 A | 4/1989 | Grollier et al. | ................. | 222/1 |
| 5,061,289 A | 10/1991 | Clausen et al. | ................ | 8/405 |
| 5,135,543 A | 8/1992 | Chan et al. | ..................... | 8/405 |
| 5,196,189 A | 3/1993 | Jacquet et al. | ................. | 424/72 |
| 5,256,526 A | 10/1993 | Suzuki et al. | ................ | 430/384 |
| 5,278,034 A | 1/1994 | Ohki et al. | ................... | 430/440 |
| 5,380,340 A | 1/1995 | Neunhoeffer et al. | ........... | 8/409 |
| 5,441,863 A | 8/1995 | Tang et al. | .................. | 430/558 |
| 5,457,210 A | 10/1995 | Kim et al. | ................ | 548/262.4 |
| 5,538,516 A | 7/1996 | Audousset et al. | ............. | 8/412 |
| 5,707,786 A | 1/1998 | Schmuck et al. | ............ | 430/373 |
| 5,708,151 A | 1/1998 | Mockli | ........................ | 534/608 |
| 5,735,908 A | 4/1998 | Cotteret et al. | ................. | 8/410 |
| 5,766,576 A | 6/1998 | Lowe et al. | .................... | 424/62 |
| 5,769,903 A | 6/1998 | Audousset et al. | ............. | 8/409 |
| 5,785,717 A | 7/1998 | Maubru et al. | ................. | 8/409 |
| 5,842,849 A | 12/1998 | Huang | ........................... | 424/70 |
| 5,851,237 A | 12/1998 | Anderson et al. | .............. | 8/409 |
| 5,876,464 A | 3/1999 | Lim et al. | ....................... | 8/409 |
| 5,993,491 A * | 11/1999 | Lim et al. | ....................... | 8/409 |
| 6,099,592 A | 8/2000 | Vidal et al. | ..................... | 8/409 |
| 6,099,593 A | 8/2000 | Terranova et al. | .............. | 8/409 |
| 6,165,230 A | 12/2000 | Rose et al. | ..................... | 8/409 |
| 6,464,731 B1 | 10/2002 | Genet et al. | .................... | 8/405 |
| 6,521,761 B2 | 2/2003 | Lim et al. | ................... | 548/557 |
| 6,613,313 B2 | 9/2003 | Kimura | ..................... | 424/70.1 |
| 6,638,321 B1 | 10/2003 | Genet et al. | .................... | 8/407 |
| 2002/0197223 A1 | 12/2002 | Kimura | ..................... | 424/70.1 |

FOREIGN PATENT DOCUMENTS

| | | |
|---|---|---|
| FR | 2 270 846 | 12/1975 |
| FR | 2 316 271 | 1/1977 |
| FR | 2 320 330 | 3/1977 |
| FR | 2 336 434 | 7/1977 |
| FR | 2 413 907 | 8/1979 |
| FR | 2 586 913 | 3/1987 |
| FR | 2 733 749 | 11/1996 |
| FR | 2 750 048 | 12/1997 |
| FR | 2 766 178 A1 | 1/1999 |
| FR | 2 801 308 | 5/2001 |
| GB | 1 021 400 | 3/1966 |
| GB | 1 026 978 | 4/1966 |
| GB | 1 153 196 | 5/1969 |
| GB | 1 458 377 | 12/1976 |
| GB | 2 239 265 | 6/1991 |
| JP | 58-42045 | 3/1983 |
| JP | 59-98437 | 6/1984 |
| JP | 59-99437 | 6/1984 |
| JP | 59-162548 | 9/1984 |
| JP | 59-171956 | 9/1984 |
| JP | 60-33552 | 2/1985 |
| JP | 60-43659 | 3/1985 |
| JP | 60-172982 | 9/1985 |
| JP | 60-190779 | 9/1985 |
| JP | 62-279337 | 12/1987 |
| JP | 88-169571 | 7/1988 |
| JP | 1-115048 | 5/1989 |
| JP | 2-19576 | 1/1990 |
| JP | 5-163124 | 6/1993 |
| JP | 6-236011 | 8/1994 |
| JP | 7-36159 | 2/1995 |
| JP | 7-84348 | 3/1995 |
| JP | 7-92632 | 4/1995 |
| JP | 7-98489 | 4/1995 |
| JP | 7-244361 | 9/1995 |
| JP | 7-3225375 | 12/1995 |
| JP | 11-158048 | 6/1999 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 98/01106 | 1/1998 |
| WO | WO 98/38175 | 9/1998 |
| WO | WO 99/03819 | 1/1999 |
| WO | WO 99/17725 | 4/1999 |
| WO | WO 01/68043 | 12/1999 |
| WO | WO 99/64417 | 12/1999 |
| WO | WO 02/45675 A1 | 6/2002 |

OTHER PUBLICATIONS

English language Derwent Abstract of DE 100 34 617, Jan. 31, 2002.

English language Derwent Abstract of DE 195 43 988, May 28, 1997.

English language Derwent Abstract of DE 23 59 399, Jun. 12, 1975.

English language Derwent Abstract of DE 299 01 593, Apr. 8, 1999.

English language Derwent Abstract of DE 299 02 262, May 6, 1999.

English language Derwent Abstract of DE 38 43 892, Jun. 28, 1990.

English language Derwent Abstract of DE 41 33 957, Apr. 15, 1993.

English language Derwent Abstract of DE 42 34 886, Apr. 21, 1994.

English language Derwent Abstract of DE 42 41 532, Jun. 16, 1994.

English language Derwent Abstract of EP 0 770 375, May, 2, 1997.

English language Derwent Abstract of EP 0 943 614, Dec. 12, 2001.

English language Derwent Abstract of FR 2 320 330, Mar. 4, 1977.

English language Derwent Abstract of FR 2 336 434, Jul. 22, 1977.

English language Derwent Abstract of FR 2 586 913, Mar. 13, 1987.

English language Derwent Abstract of FR 2 733 749, Nov. 8, 1996.

English language Derwent Abstract of FR 2 750 048, Dec. 26, 1997.

English language Derwent Abstract of FR 2 766 178, Jan 22, 1999.

English language Derwent Abstract of FR 2 801 308, May 25, 2001.

English language Derwent Abstract of JP 1–115048, May 8, 1989.

English language Derwent Abstract of JP 11–158048, Jun. 15, 1999.

English language Derwent Abstract of JP 2–19576, Jan. 23, 1990.

English language Derwent Abstract of JP 5–163124, Jun. 19, 1993.
English language Derwent Abstract of JP 58042045, Mar. 11, 1983.
English language Derwent Abstract of JP 5999437, Jun. 8, 1984.
English language Derwent Abstract of JP 60190779, Sep. 28, 1985.
English language Derwent Abstract of JP 6033552, Feb. 20, 1985.
English language Derwent Abstract of JP 6043659, Mar. 8, 1985.
English language Derwent Abstract of JP 62279337, Dec. 4, 1987.
English language Derwent Abstract of JP 6236011, Aug. 23, 1994.
English language Derwent Abstract of JP 7036159, Feb. 7, 1995.
English language Derwent Abstract of JP 7084348, Mar. 31, 1995.
English language Derwent Abstract of JP 7092632, Apr. 7, 1995.
English language Derwent Abstract of JP 7098489, Apr. 11, 1995.
English language Derwent Abstract of JP 7244361, Sep. 19, 1995.
English language Derwent Abstract of JP 7325375, Dec. 12, 1995.
English language Derwent Abstract of JP application 88–169571.
Eser llhan, et al., "Synthese von 6–Benzyliden–2–(a,a–diphenyl–a–hydroxyacetyl)–thiazolo[3,2–b]–s–frialzol–5–onen als potentiell biologisch wirksame Stroffe", Archiv der Pharmazie, pp. 825–826, 1994.
French Search Report for FR 02/03847, Examiner Seitner, Nov. 25, 2002.
French Search Report for FR 02/07939, Examiner Seitner, Feb. 17, 2003.
French Search Report for FR 02/08514, Examiner Krische, Mar. 20, 2003.
French Search Report for FR 02/11133, Examiner Seitner, May 15, 2003.
G. Fonnum et al., "Associative thickeners. Part I: Synthesis, rheology and aggregation behavior", Colloid & Polymer Science, 271, pp. 380–389, 1993.
Giuliana Cardillo et al., "Sulle 1,2–difenil–3,5–dichetopirazolidine", Gazzetta Chimica Italiana, vol. 96, pp. 973–985, 1966.
H. Koopman, :"Investigations on Herbicides IV, The synthesis of 2,6–dichlorobenzonitrile", Recueil, pp. 1075–1083, 1961.
Hans Beyer et al., "Uber die Pyrazolbidung aus alpha–Chlor–acetessigester und Thiocarbohydrazid," Chemische Berichte, pp 2550–2555, 1956.
Henryk Foks et al., "Synthesis and Biological Activity of Thiazolo–1,2,4–Triazoles", Acta Poloniae Pharmaceutica–Drug Research, pp. 415–420, 1995.
International Search Report for PCT/FR 01/03540, Examiner Glikman, Mar. 11, 2002.
International Search Report for PCT/FR 01/03541, Examiner Glikman, Mar. 11, 2002.
International Search Report for PCT/FR 01/03542, Examiner Glikman, Mar. 11, 2002.

International Search Report for PCT/FR 01/03543, Examiner Voyiazoglou, Mar. 14, 2002.
International Search Report for PCT/FR 01/03571, Examiner Glikman, Mar. 11, 2002.
Joseph Bailey, "Synthesis of 1 H–Pyrazolo[3,2–c]–s–Triazoles and Derived Azamethine Dyes," Journal of The Chemical Society, pp 2047–2052, 1977.
Lidia Wyzgowska, et al., "O Reakcjach Trikarboetoksymetanu", Acta Poloniae Pharmaceutica, pp, 83–88, 1982.
Mohamed Ali et al., "Reactions with Thiazolo[3,2–b]–s–triazol–3(2H)–ones", Journal Für Praktische Chemie, pp. 12–18, 1976.
Mohamed Elnagdi et al., "Routes for the Synthesis of 3,5–Diaminopyrazoles, 2–Aminopyrazolo[1,5–a]pyrimidines and 5–Aminopyrazolo[1,5–]pyrimidines", Journal Für Praktische Chemie, pp. 533–538, 1978.
Mohamed Elnagdi et al., "Studies on 3,5–pyrazolidinediones. IV. Addition of 4–Arylazo–3,5–pyrazolidinediones to Ethyl Acrylate", Bulletin of the Chemical Society of Japan, vol. 46, 1973. pp. 1830–1833.
Office Action in co–pending Application No. 09/656,913 dated Dec. 14, 2004 (Ex. Elhilo).
Office Action in co–pending Application No. 09/959,913 dated Dec. 16, 2003 (Ex. Elhilo).
Office Action in co–pending Application No. 10/433,411 dated Sep. 9, 2004 (Ex. Elhilo).
Office Action in co–pending Application No. 10/433,687 dated Sep. 14, 2004 (Ex. Elhilo).
Office Action in co–pending Application No. 10/433,688 dated Sep. 9, 2004 (Ex. Elhilo).
Office Action in co–pending Application No. 10/433,689 dated Oct. 26, 2004 (Ex. Elhilo).
Paul Carter et al., "Studies on the Synthesis of Antitumor Agent CC1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, pp. 2711–2717, 1987.
Philip Magnus et al., "Synthesis of Helical Poly–b–pyrroles. Multiple Atropisomerism Resulting in Helical Enantiomorphic Conformations", Journal of the American Chemical Society, pp. 2465–2468, 1990.
R. Stollé, "Ueber die Ueberführung der secundären Säurehydrazide in Derivate des Furodiazols, Pyrrodiazols und Thiodiazols", Berichte Der Deutschen Chemischen Gesellschaft, pp. 797–798, 1899.
R.L. Bent et al., "Chemical Constitution, Electrochemical, Photographic and Allergenic Properties of p–Amino–N–dialkylanilines," Journal of the American Chemical Society, vol. 73, No. 7, Jul. 1951, pp. 3100–3125.
S. Hiller et al., "Electron Density Distribution In Hetrocyclic Systems With Two Adjacent Nitrogen Atoms", Chemistry of Heterocyclic Compounds, pp. 93–96, 1965.
Thomas Kauffman et al., "Synthese von Amidrazonen aus Nitrilen und Natriumhydrazid", Chemische Berichte, pp 3436–3443, 1964.
Victor Cohen, "A New Method of Synthesis of Some 2–Aryl and 2–Heterocyclic Benzimidazole, Benzoxazole and Benzothiazole Derivatives", Journal of Heterocyclic Chemistry, 16, pp. 13–16, 1979.

* cited by examiner

BIS-PARA-PHENYLENEDIAMINE DERIVATIVES COMPRISING A PYRROLIDYL GROUP AND USE OF THESE DERIVATIVES FOR DYEING KERATIN FIBRES

This application claims benefit of U.S. Provisional Application No. 60/431,713, filed Dec. 9, 2002.

The disclosure herein relates to novel bis-para-phenylenediamine derivatives comprising a pyrrolidyl group, as well as to dye compositions comprising the derivatives disclosed herein, and to the process of dyeing keratin fibres using these compositions.

It is known practice to dye keratin fibres, for example human hair, with dye compositions containing oxidation dye precursors, such as ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives and 5,6-dihydroxyindoline derivatives, which are generally known as oxidation bases. Oxidation dye precursors, or oxidation bases, are colourless or weakly coloured compounds that, when combined with oxidizing products, may give rise to coloured compounds and dyes by a process of oxidative condensation.

It is also known that the shades obtained with these oxidation bases may be varied by combining them with couplers or coloration modifiers, the latter being chosen, for example, from aromatic meta-diamines, meta-aminophenols, meta-hydroxyphenols and certain heterocyclic compounds, for instance pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used as oxidation bases and couplers allows a wide range of colours to be obtained.

The "permanent" coloration obtained using oxidation dyes may satisfy a certain number of requirements. It should have no toxicological drawback, be capable of producing shades in the desired intensity, and it show good resistance to external agents (such as, light, bad weather, washing, permanent-waving, perspiration and rubbing).

The dyes can also be able to cover grey hair and they can be as unselective as possible, i.e. they can produce the smallest possible differences in coloration along the same keratin fibre, which may in fact be differently sensitized (i.e. damaged) between its end and its root. They can also show good chemical stability in formulations and have a good toxicological profile.

In the field of hair dyeing, para-phenylenediamine and para-tolylenediamine are oxidation bases that are widely used. They make it possible with oxidation couplers to obtain varied shades.

However, there is a need for new oxidation bases that have a better toxicological profile than para-phenylenediamine and para-tolylenediamine, while at the same time giving the hair excellent properties in terms of colour intensity, variety of shade, colour uniformity and resistance to external agents.

It is known practice to use para-phenylenediamine derivatives substituted with a pyrrolidine group as oxidation bases for colouring keratin fibres. For example, patent U.S. Pat. No. 5,851,237 describes the use of 1-(4-aminophenyl) pyrrolidine derivatives optionally substituted on the benzene nucleus, as replacements for para-phenylenediamine. U.S. Pat. No. 5,993,491 proposes the use of N-(4-aminophenyl)-2-hydroxymethylpyrrolidine derivatives optionally substituted on the benzene nucleus and on the pyrrolidine heterocycle, in position 4, with a hydroxyl radical, as replacement for para-phenylenediamine. U.S. Pat. No. 5,876,464 describes para-phenylenediamine derivatives substituted with a pyrrolidine group bearing a carbamoyl radical in position 2.

Patent application JP 11-158 048 proposes compositions containing at least one compound chosen from 4-aminoaniline derivatives optionally substituted on the benzene nucleus, one of the nitrogen atoms of which is included in a 5- to 7-membered carbon-based ring. Document WO 02/45675 describes para-phenylenediamine derivatives substituted with a pyrrolidine radical bearing a particular quaternary ammonium group.

It is clearly established that these previously proposed compounds cannot give the hair a coloration equivalent in quality to that obtained with para-phenylenediamine or with para-tolylenediamine, due to the lack of colour intensity and colour uniformity.

There is thus a real need to discover novel oxidation bases that have both a good toxicological profile and properties such that the compositions comprising them can give the hair excellent properties in terms of colour intensity, variety of shades, colour uniformity and resistance to the various external attacks to which the hair may be subjected.

Disclosed herein are novel dye compositions that do not have some of the drawbacks of the oxidation bases of the prior art, and are suitable for dyeing keratin fibres that are capable of producing intense colorations in varied shades, which can be sparingly selective and particularly resistant, and which have a good toxicological profile.

Thus, one aspect of the disclosure herein is bis-para-phenylenediamine derivatives substituted with a pyrrolidyl group, wherein the derivatives are chosen from those of formula (I), and the addition salts thereof:

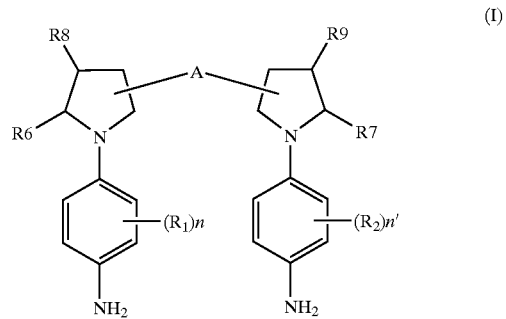

wherein:

n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms, and $C_1$–$C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or diazo, nitro, or nitroso radicals, and wherein the chain may be substituted with at least one entity chosen from halogen atoms and hydroxyl, $C_1$–$C_6$ alkoxy, amino, mono-, di($C_1$–$C_6$)alkylamino and tri($C_1$–$C_6$)alkylammonium radicals, and N—($C_1$–$C_6$)alkylimidazolinium radicals;

A is chosen from a covalent bond, and alkylene chains comprising from 1 to 14 carbon atoms, wherein the chains may be linear, branched, saturated or unsaturated, and wherein at least one of the carbon atoms of the chain may optionally be replaced with an entity chosen from: onium radical Z, oxygen, sulphur, silicon and nitrogen atoms, and CO, SO, and $SO_2$ groups, wherein the alkylene chains may optionally be substituted with at least one entity chosen from: halogen atoms, hydroxyl, $C_1$–$C_6$ alkoxy, amino, ($C_1$–$C_6$)alkylamino, and di($C_1$–$C_6$)alkylamino radicals;

$R_6$ and $R_7$, which may be identical or different, are chosen from: hydrogen atoms; carboxyl radicals; ($C_1$–$C_4$) alkylcarboxyl radicals; carbamoyl radicals; ($C_1$–$C_4$) (alkyl)carbamoyl radicals; (dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated, and/or substituted with at least one entity chosen from hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from carboxylic, ($C_1$–$C_6$)alkylcarbonyl, ($C_1$–$C_6$) alkoxycarbonyl, carbamoyl, mono- or di($C_1$–$C_6$) alkylcarbamoyl, tri($C_1$–$C_6$)alkylsilane, tri(($C_1$–$C_6$)alkyl) ammonium and N—($C_1$–$C_6$)alkylimidazolinium radicals;

$R_8$ and $R_9$, which may be identical or different, are chosen from: hydrogen atoms; hydroxyl radicals; ($C_1$–$C_4$) alkyloxy radicals; amino radicals; mono- and di($C_1$–$C_4$) alkylamino radicals; thiol radicals; carboxyl radicals; ($C_1$–$C_4$)alkylcarboxyl radicals; carbamoyl radicals; ($C_1$–$C_4$)(alkyl and/or dialkyl)carbamoyl radicals; tri ($C_1$–$C_6$)alkylsilane radicals; tri(($C_1$–$C_6$)alkyl)ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from: hydroxyl, ($C_1$–$C_6$)alkyloxy, amino, mono- and/or di($C_1$–$C_6$)alkylamino, thiol, and ($C_1$–$C_6$)alkylsulphonic radicals, and halogen atoms; $C_1$–$C_{15}$ alkyl radicals which may optionally be unsaturated, and/or substituted with at least one radical chosen from: carboxylic, ($C_1$–$C_6$)alkylcarbonyl, ($C_1$–$C_6$) alkoxycarbonyl, carbamoyl, mono- and/or di($C_1$–$C_6$) alkylcarbamoyl, tri($C_1$–$C_6$)alkylsilane, tri(($C_1$–$C_6$)alkyl) ammonium, and N—($C_1$–$C_6$)alkylimidazolinium radicals.

Also disclosed herein is a dye composition comprising at least one bis-para-phenylenediamine derivative of formula (I) as an oxidation base. Still further disclosed herein is the use of this composition for dyeing keratin fibres, as well as a process for dyeing keratin fibres, for example, human keratin fibres such as the hair, using the composition of the present invention.

The composition of the present disclosure makes it possible, for instance, to obtain chromatic, powerful, sparingly selective and colourfast coloration of keratin fibres.

In the context of the present disclosure, an aliphatic hydrocarbon-based chain can be a linear or branched chain that may contain unsaturations of alkene or alkyne type. An alicyclic hydrocarbon-based chain is a saturated or unsaturated branched chain containing no aromatic cyclic structure.

When the chain is interrupted with an oxygen, sulphur, nitrogen or silicon atom T or $SO_2$, a unit $CH_2$-T-$CH_2$, -T-, etc. is obtained, for example.

By way of example, $R_1$ and $R_2$, which may be identical or different, may be chosen from chlorine and bromine atoms, and methyl, ethyl, isopropyl, vinyl, allyl, methoxymethyl, hydroxyethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy and 2-hydroxyethyloxy radicals.

According to one aspect of the disclosure, $R_1$ and $R_2$, which may be identical or different, are chosen from chlorine, bromine, $C_1$–$C_4$ alkyl radicals, $C_1$–$C_4$ hydroxyalkyl radicals, $C_1$–$C_4$ aminoalkyl radicals, $C_1$–$C_4$ alkoxy radicals, $C_1$–$C_4$ hydroxyalkoxy radicals, tri($C_1$–$C_4$) alkylammonium($C_1$–$C_4$)alkyl radicals and N—($C_1$–$C_4$) alkylimidazolinium($C_1$–$C_4$)alkyl radicals. For example, $R_1$ and $R_2$ can chosen from methyl, isopropyl, tert-butyl, hydroxymethyl, 2-hydroxyethyl, 1,2-dihydroxyethyl, methoxy, isopropyloxy, 2-hydroxyethoxy, trimethylammoniummethyl and N-methylimidazolinium radicals.

In formula (I), n and n' are independently 0 or 1.

According to another aspect of the disclosure, A does not comprise a peroxide bond, or a diazo, nitro or nitroso radical.

A can be, for example, a covalent bond or an alkylene chain containing from 1 to 8 carbon atoms. According to another aspect of the disclosure, A is an alkylene chain comprising from 1 to 8 carbon atoms, wherein one or more of the carbon atoms of the chain can optionally be replaced with a nitrogen atom and/or an oxygen atom. A can represent an alkylene chain, one or more of the carbon atoms of which chain may be replaced with a nitrogen atom and/or an oxygen atom, and comprising one or more onium radicals Z.

The term "onium" means a nitrogen-based quaternary radical.

According to one aspect of the disclosure, the onium radical Z corresponds to formula (II):

wherein:

$Y^-$ is a counterion;

$R_3$ and $R_4$, which may be identical or different, are chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$) alkoxy($C_1$–$C_6$)alkyl radicals; aryl radicals; benzyl radicals; amido($C_1$–$C_6$)alkyl radicals; tri($C_1$–$C_6$) alkylsilane($C_1$–$C_6$)alkyl radicals; $C_1$–$C_6$ aminoalkyl radicals; $C_1$–$C_6$ aminoalkyl radicals, wherein the amines are mono- and/or disubstituted with at least one entity chosen from $C_1$–$C_4$ alkyl, ($C_1$–$C_6$)alkylcarbonyl, amido and ($C_1$–$C_6$)alkylsulphonyl radicals;

$R_3$ and $R_4$, together with the nitrogen atom to which they are attached, form a 5-, 6- or 7-membered heterocycle; and when at least two onium radicals of formula (II) are present in the chain A, at least one of the radicals $R_3$ and $R_4$ of one of the onium radicals may form a cyclic diammonium structure with at least one of the radicals $R_3$ and $R_4$ of the at least one other onium radical.

In the latter case, the structures that are obtained by linking together two groups $R_3$ or $R_4$ of two onium radicals present in chain A are, for example:

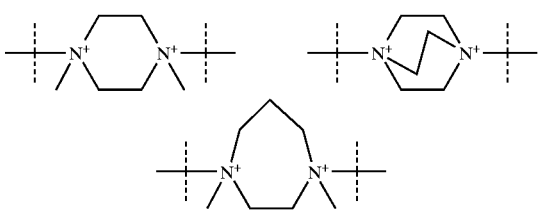

$R_3$ and $R_4$, which may be identical or different, may be chosen, for example, from $C_1$–$C_4$ alkyl radicals and $C_1$–$C_4$ hydroxyalkyl radicals. They may also together form a cationic pyrrolidinium, piperidinium, piperazinium or morpholinium ring, the cationic ring possibly being substituted with an entity chosen from halogen atoms and hydroxyl, $C_1$–$C_6$ alkyl, $C_1$–$C_6$ monohydroxyalkyl, $C_2$–$C_6$ polyhydroxyalkyl, $C_1$–$C_6$ alkoxy, tri($C_1$–$C_6$)alkylsilane($C_1$–$C_6$)alkyl, amido, carboxyl, ($C_1$–$C_6$)alkyl, thio, $C_1$–$C_6$ thioalkyl, ($C_1$–$C_6$) alkylthio, amino, amino mono- or disubstituted with a ($C_1$–$C_6$)alkyl radical, ($C_1$–$C_6$)alkylcarbonyl, amido and ($C_1$–$C_6$)alkylsulphonyl radicals. By way of example, $R_3$ and $R_4$ together may form a cationic pyrrolidinium, piperidinium or morpholinium ring.

The onium radical Z may also be a radical of formula (III):

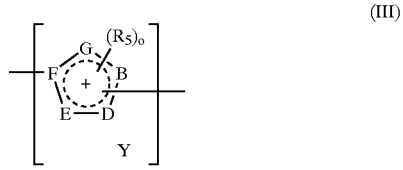

(III)

wherein:

the ring members B, D, E, F and G, which may be identical or different, are chosen from carbon, oxygen, sulphur and nitrogen atoms, such that B, D, E, F, and G are selected so as to form an aromatic ring cationized on the nitrogen, wherein the ring is chosen from pyrolium, pyrazolium, imidazolium, triazolium, oxazolium, isoxazolium, thiazolium and isothiazolium rings;

o is an integer ranging from 0 to 4;

$R_5$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane ($C_1$–$C_6$)alkyl radicals, ($C_1$–$C_6$)alkoxy($C_1$–$C_6$)alkyl radicals, carbamyl($C_1$–$C_6$)alkyl radicals, ($C_1$–$C_6$) alkylcarboxy($C_1$–$C_6$)alkyl radicals and benzyl radicals; and further wherein the at least one radical $R_5$ is attached to a carbon, $R_5$ may also be a radical chosen from hydroxyl, ($C_1$–$C_4$)alkyloxy, amino, ($C_1$–$C_4$)alkylamino and di($C_1$–$C_4$)alkylamino radicals, and $Y^-$ is a counterion.

In one aspect of the disclosure, for example, Z is chosen from an imidazolium ring and a thiazolium ring.

The onium radical Z may also be a radical of formula (IV):

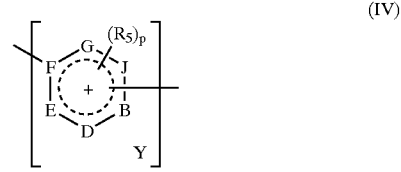

(IV)

wherein:

the ring members B, D, E, F, G and J, which may be identical or different, are chosen from carbon and nitrogen atoms, such that B, D, E, F, G, and J are selected so as to form an aromatic ring cationized on the nitrogen, wherein the ring is chosen from pyridinium, pyrimidinium, pyrazinium, triazinium and pyridaziniumrings;

p is an integer from 0 to 4;

$R_5$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane ($C_1$–$C_6$)alkyl radicals, ($C_1$–$C_6$)alkoxy($C_1$–$C_6$)alkyl radicals, carbamyl($C_1$–$C_6$)alkyl radicals, ($C_1$–$C_6$) alkylcarboxy($C_1$–$C_6$)alkyl radicals and benzyl radicals; and where the at least one radical $R_5$ is attached to a ring member chosen from carbon, $R_5$ may optionally be a radical chosen from hydroxyl, ($C_1$–$C_4$)alkyloxy, ($C_1$–$C_4$) alkylamino and di($C_1$–$C_4$)alkylamino radicals, and $Y^-$ represents a counterion.

In another aspect of this disclosure, the onium radical Z of formula (IV) is, for instance, a cationized pyridinium ring.

In the context of the present disclosure, $R_5$ is, for example, a $C_1$–$C_4$ alkyl or $C_1$–$C_4$ hydroxyalkyl radical.

By way of non-limiting illustration, $R_6$ and $R_7$ may be chosen from hydrogen, a $C_1$–$C_4$ hydroxyalkyl radical, for example hydroxymethyl, a $C_1$–$C_4$ alkyl radical, for example methyl, a carboxyl radical, a carbamoyl radical, a mono- or di($C_1$–$C_4$)alkylcarbamoyl radical, for example N,N-dimethylcarbamoyl, a tri($C_1$–$C_4$)alkylammonium($C_1$–$C_4$) alkyl radical, for example trimethylammoniummethyl, or an N—($C_1$–$C_4$)alkylimidazolium($C_1$–$C_4$)alkyl radical.

For further example, $R_8$ and $R_9$ may chosen from hydrogen, a hydroxyl radical, an amino radical, a mono- or di($C_1$–$C_4$)alkylamino radical, for example dimethylamino or bis(2-hydroxyethyl)amino, a $C_1$–$C_4$ alkyl radical, for example methyl, a tri($C_1$–$C_4$)alkylammonium radical, for example trimethylammonium, or an N—($C_1$–$C_4$) alkylimidazolinium radical, for example N-methylimidazolinium.

According to another aspect of the disclosure, the derivatives of the invention are chosen from those of formula (I') below

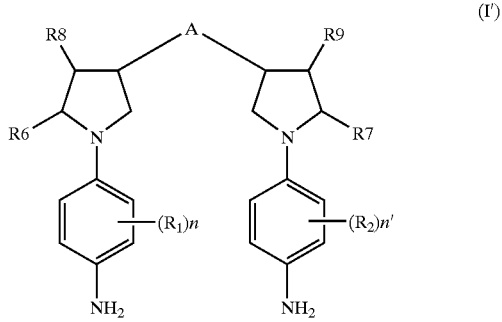

(I')

wherein $R_1$, $R_2$, n, n', $R_6$, $R_7$, $R_8$, $R_9$ and A are as defined above.

Mention may be made, in formula (I'), of the following examples: n and n' may be 0 or 1, $R_1$ and $R_2$ may be chosen from methyl, isopropyl, tert-butyl, hydroxymethyl, 2-hydroxyethyl, 1,2-dihydroxyethyl, methoxy, isopropoxy, 2-hydroxyethoxy and trimethylammoniummethyl radicals and an N-methylimidazoliniummethyl radical, $R_6$ and $R_7$ may be chosen from a hydrogen atom, $C_1$–$C_4$ hydroxyalkyl, for example hydroxymethyl, a $C_1$–$C_4$ alkyl radical, for example methyl, a carboxyl radical, a carbamoyl radical, a mono- or di($C_1$–$C_4$)alkylcarbamoyl radical, for example N,N-dimethylcarbamoyl, a tri($C_1$–$C_4$)alkylammonium ($C_1$–$C_4$)alkyl radical, for example trimethylammoniummethyl, and an N-alkyl($C_1$–$C_4$) imidazoliumalkyl radical, $R_8$ and $R_9$ may be chosen from a hydrogen atom, a hydroxyl radical, an amino radical, a mono- or di(($C_1$–$C_4$)alkyl)amino radical, for example dimethylamino or bis(2-hydroxyethyl)amino, a $C_1$–$C_4$ alkyl radical, for example methyl, a tri($C_1$–$C_4$)alkylammonium radical, for example trimethylammonium, and an N—($C_1$–$C_4$)alkylimidazolinium radical, for example N-methylimidazolinium, A may be chosen from a covalent bond or a radical chosen from:

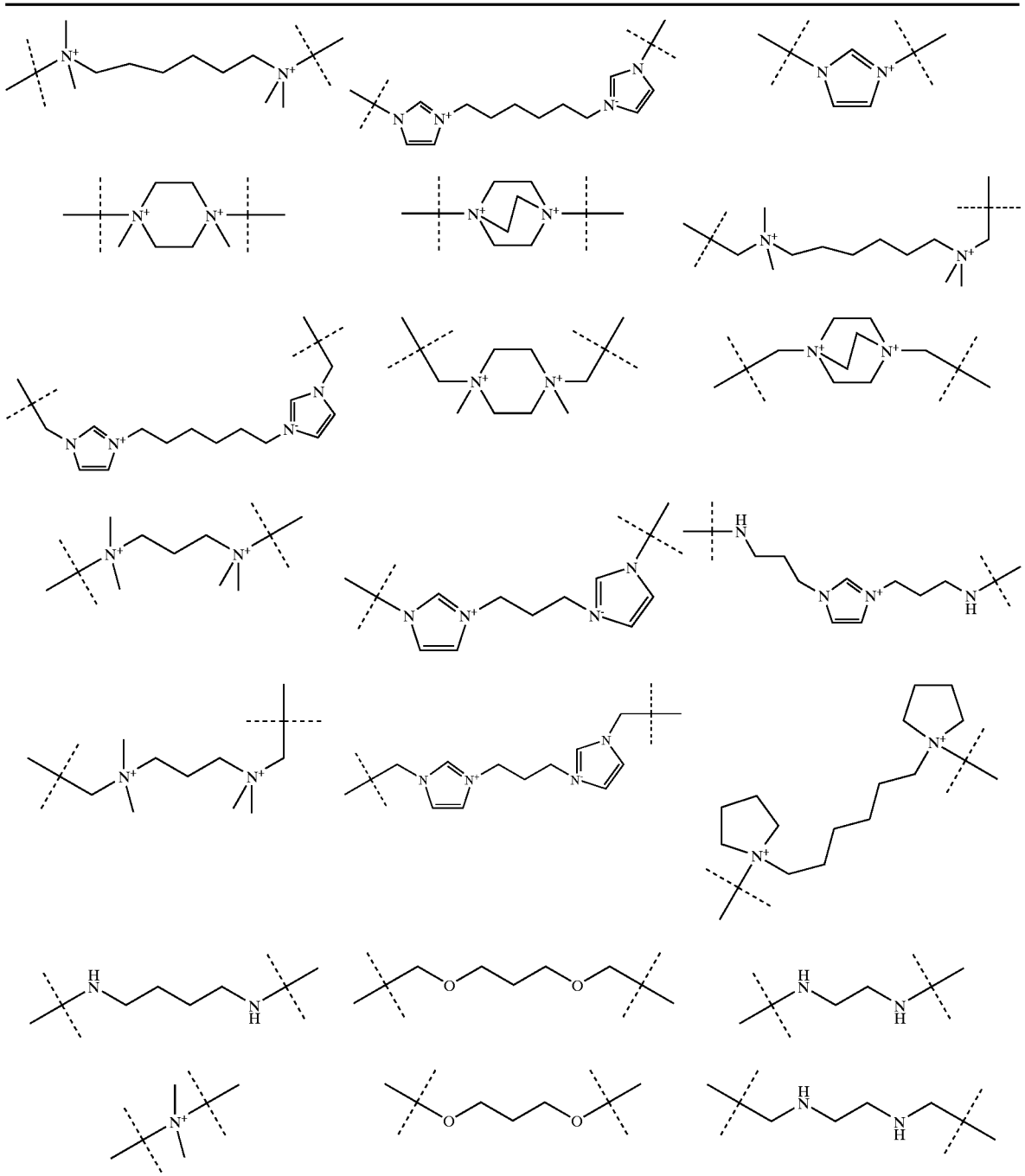

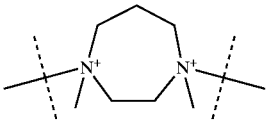

In the context of the present disclosure, the counterion Y may be chosen from halogen atoms, such as bromine, chlorine, fluorine and iodine, hydroxides, citrates, succinates, tartrates, lactates, tosylates, mesylates, benzenesulphonates, acetates, hydrogen sulphates and $C_1$–$C_6$ alkyl sulphates, for instance methyl sulphate and/or ethyl sulphate.

Non-limiting examples of derivatives of formula (I) that may be mentioned include:

| Structure | Nomenclature |
| --- | --- |
| 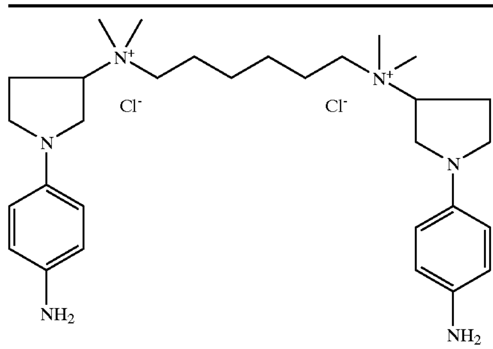 | N,N'-bis[1-(4-aminophenyl)pyrrolidin-3-yl]-N,N,N',N'-tetramethylhexane-1,6-diaminium dichloride |
| 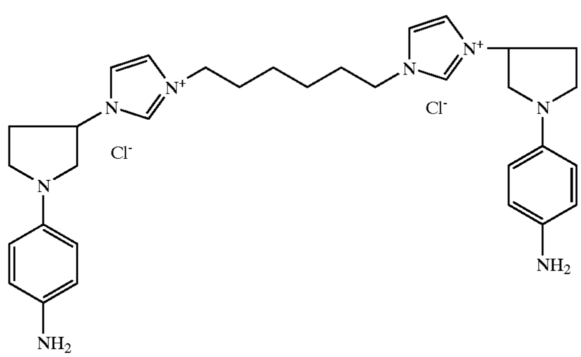 | 3-[1-(4-aminophenyl)pyrrolidin-3-yl]-1-(6-{1-[1-(4-aminophenyl)pyrrolidin-3-yl]-1H-imidazol-3-ium-3-yl}hexyl)-1H-imidazol-3-ium dichloride |
| 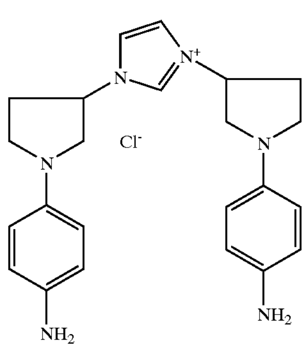 | 1,3-bis[1-(4-aminophenyl)pyrrolidin-3-yl]-1H-imidazol-3-ium chloride |

| Structure | Nomenclature |
|---|---|
| | 1,4-bis[1-(4-aminophenyl)pyrrolidin-3-yl]-1,4-dimethylpiperazinediium dichloride |
| 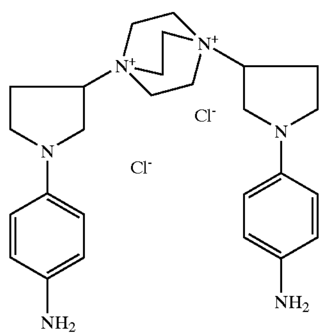 | 1,4-bis[1-(4-aminophenyl)pyrrolidin-3-yl]-1,4-diazoniabicyclo[2.2.2]octane dichloride |
| 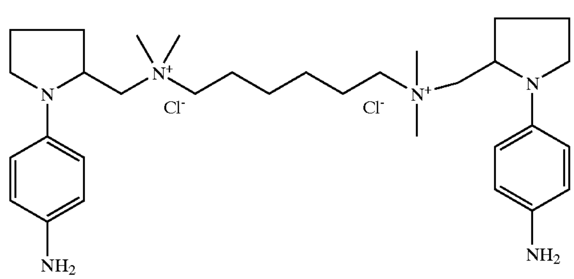 | N,N'-bis{[1-(4-aminophenyl)pyrrolidin-2-yl]methyl}-N,N,N',N'-tetramethylhexane-1,6-diaminium dichloride |
| 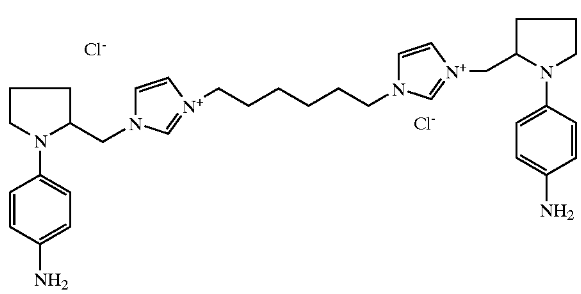 | 3-{[1-(4-aminophenyl)pyrrolidin-2-yl]methyl}-1-[6-(1-{[1-(4-aminophenyl)pyrrolidin-2-yl]methyl}-1H-imidazol-3-ium-3-yl)hexyl]-1H-imidazol-3-ium dichloride |
| 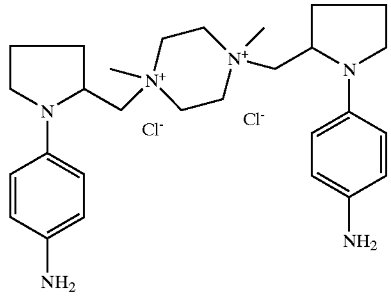 | 1,4-bis{[1-(4-aminophenyl)pyrrolidin-2-yl]methyl}-1,4-dimethylpiperazinediium dichloride |

-continued

| Structure | Nomenclature |
|---|---|
| 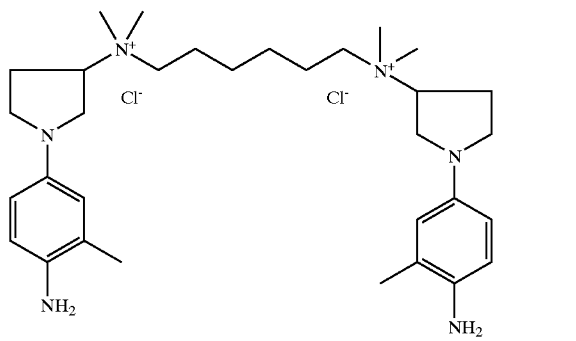 | N,N'-bis[1-(4-amino-3-methylphenyl)pyrrolidin-3-yl]-N,N,N',N'-tetramethylhexane-1,6-diaminium dichloride |
| 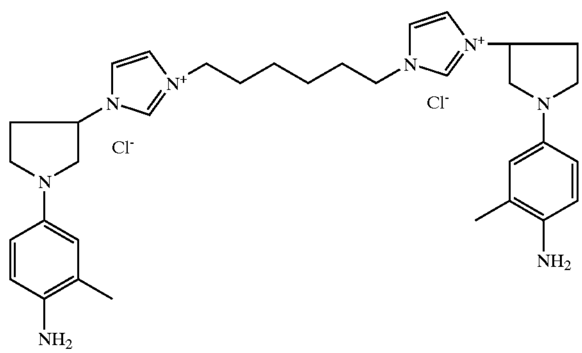 | 3-[1-(4-amino-3-methylphenyl)pyrrolidin-3-yl]-1-(6-{1-[1-(4-amino-3-methylphenyl)pyrrolidin-3-yl]-1H-imidazol-3-ium-3-yl}hexyl)-1H-imidazol-3-ium dichloride |
| 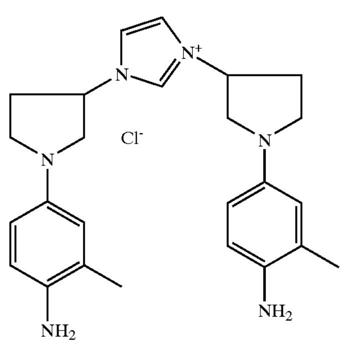 | 1,3-bis[1-(4-amino-3-methylphenyl)pyrrolidin-3-yl]-1H-imidazol-3-ium chloride |
| 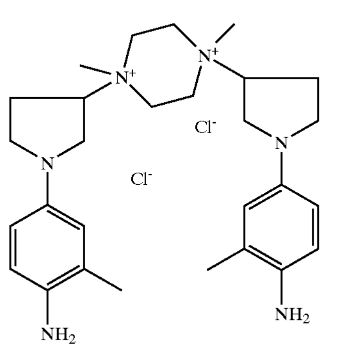 | 1,4-bis[1-(4-amino-3-methylphenyl)pyrrolidin-3-yl]-1,4-dimethylpiperazinediium dichloride |

-continued

| Structure | Nomenclature |
|---|---|
| 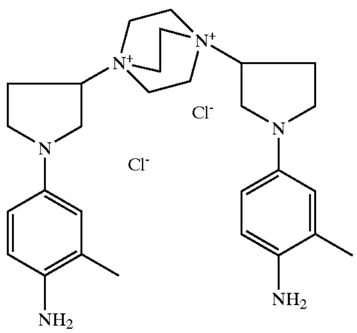 | 1,4-bis[1-(4-amino-3-methylphenyl)pyrrolidin-3-yl)-1,4-diazoniabicyclo[2.2.2]octane dichloride |
| 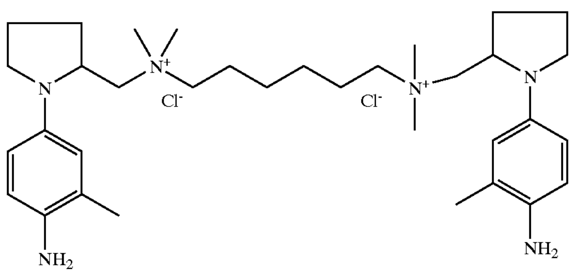 | N,N'-bis{[1-(4-amino-3-methylphenyl)pyrrolidin-2-yl]methyl}-N,N,N',N'-tetramethylhexane-1,6-diaminium dichloride |
| 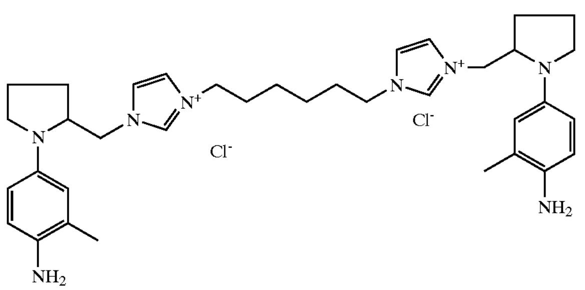 | 3-{[1-(4-amino-3-methylphenyl)pyrrolidin-2-yl]methyl}-1-[6-(1-{[1-(4-amino-3-methylphenyl)pyrrolidin-2-yl]methyl}-1H-imidazol-3-ium-3-yl)hexyl]-1H-imidazol-3-ium dichloride |
| 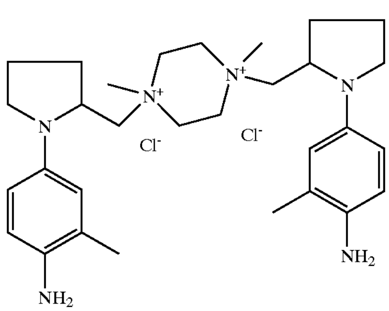 | 1,4-bis{[1-(4-amino-3-methylphenyl)pyrrolidin-2-yl]methyl}-1,4-dimethylpiperazinediium dichloride |
| 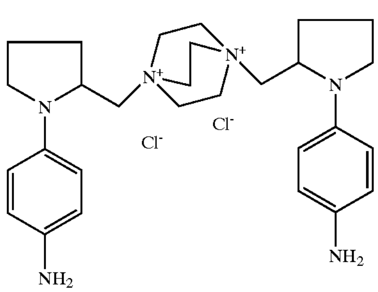 | 1,4-bis{[1-(4-aminophenyl)pyrrolidin-2-yl]methyl}-1,4-diazoniabicyclo[2.2.2]octane dichloride |

-continued

| Structure | Nomenclature |
|---|---|
| 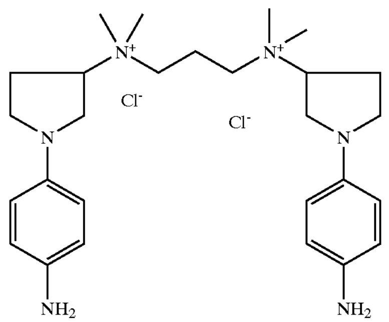 | N,N'-bis[1-(4-aminophenyl)pyrrolidin-3-yl]-N,N,N',N'-tetramethylpropane-1,3-diaminium dichloride |
| 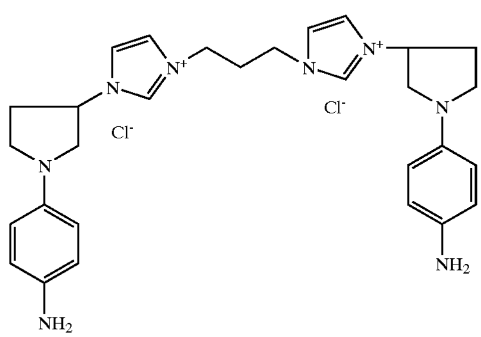 | 3-[1-(4-aminophenyl)pyrrolidin-3-yl]-1-(3-{1-[1-(4-aminophenyl)pyrrolidin-3-yl]-1H-imidazol-3-ium-3-yl}propyl)-1H-imidazol-3-ium dichloride |
| 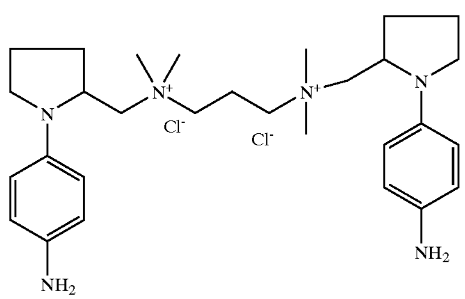 | N,N'-bis{[1-(4-aminophenyl)pyrrolidin-2-yl]methyl}-N,N,N',N'-tetramethylpropane-1,3-diaminium dichloride |
| 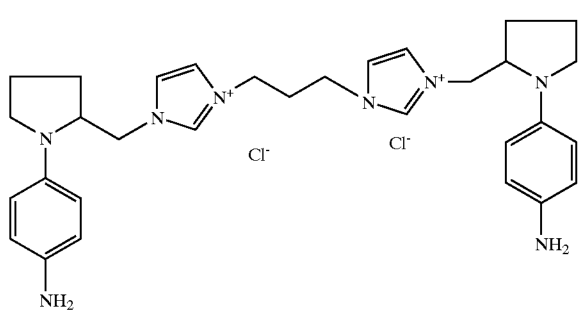 | 3-{[1-(4-aminophenyl)pyrrolidin-2-yl]methyl}-1-[3-(1-{[1-(4-aminophenyl)pyrrolidin-2-yl]methyl}-1H-imidazol-3-ium-3-yl)propyl]-1H-imidazol-3-ium dichloride |

-continued

| Structure | Nomenclature |
|---|---|
| 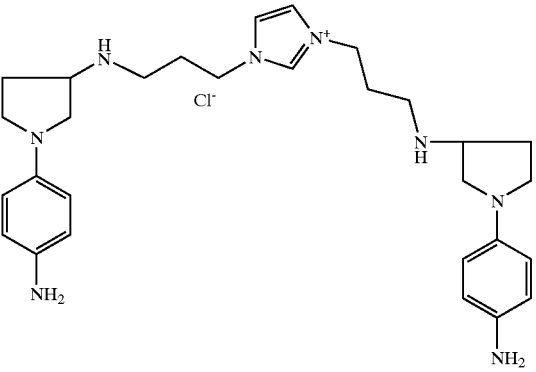 | 1,3-bis(3-{[1-(4-aminophenyl)pyrrolidin-3-yl]amino}propyl)-1H-imidazol-3-ium chloride |
| 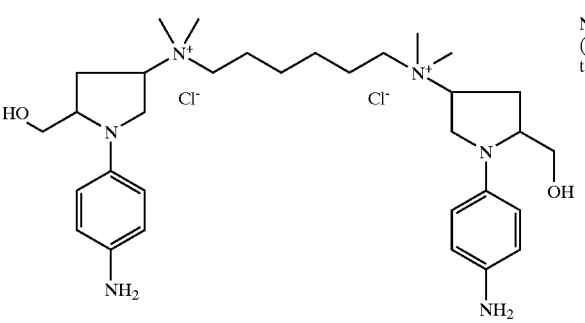 | N,N'-bis[1-(4-aminophenyl)-5-(hydroxymethyl)pyrrolidin-3-yl]-N,N,N',N'-tetramethylhexane-1,6-diaminium dichloride |
| 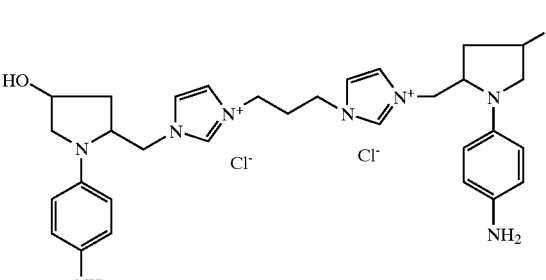 | 3-{[1-(4-aminophenyl)-4-hydroxypyrrolidin-2-yl]methyl}-1-[3-(1-{[1-(4-aminophenyl)-4-hydroxypyrrolidin-2-yl]methyl}-1H-imidazol-3-ium-3-yl)propyl]-1H-imidazol-3-ium dichloride |
| 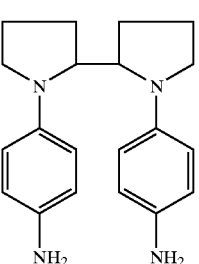 | 4-[1'-(4-aminophenyl)-2,2'-bipyrrolidin-1-yl]phenylamine |
| 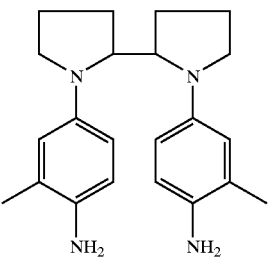 | 4-[1'-(4-amino-3-méthylphenyl)-2,2'-bipyrrolidin-1-yl]phenylamine |

-continued

| Structure | Nomenclature |
|---|---|
| 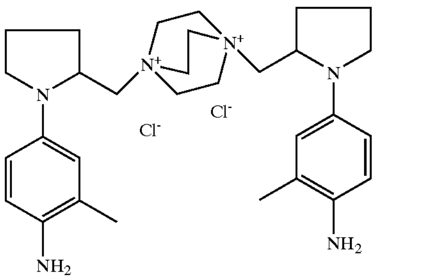 | 1,4-bis{[1-(4-amino-3-methylphenyl)pyrrolidin-2-yl]methyl}-1,4-diazoniabicyclo[2.2.2]octane dichloride |
| 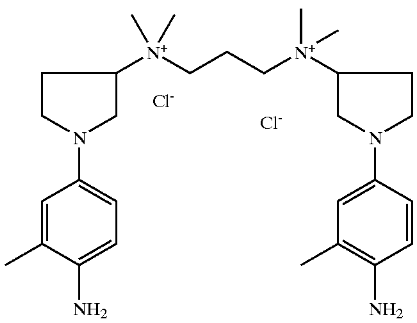 | N,N'-bis[1-(4-amino-3-methylphenyl)pyrrolidin-3-yl]-N,N,N',N'-tetramethylpropane-1,3-diaminium dichloride |
| 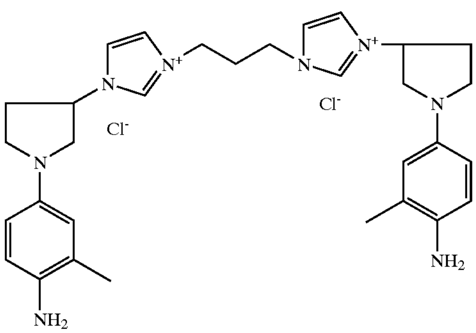 | 3-[1-(4-amino-3-methylphenyl)pyrrolidin-3-yl]-1-(3-{1-[1-(4-amino-3-methylphenyl)pyrrolidin-3-yl]-1H-imidazol-3-ium-3-yl}propyl)-1H-imidazol-3-ium dichloride |
| 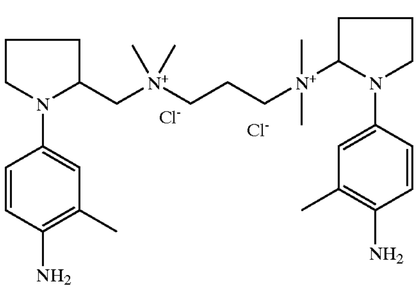 | N,N'-bis{[1-(4-amino-3-methylphenyl)pyrrolidin-2-yl]methyl}-N,N,N',N'-tetramethylpropane-1,3-diaminium dichloride |
| 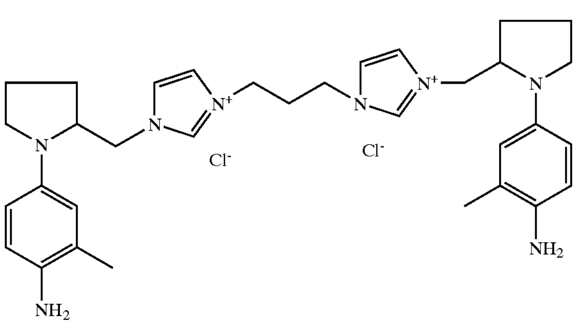 | 3-{[1-(4-amino-3-methylphenyl)pyrrolidin-2-yl]methyl}-1-[3-(1-{[1-(4-amino-3-methylphenyl)pyrrolidin-2-yl]methyl}-1H-imidazol-3-ium-3-yl)propyl]-1H-imidazol-3-ium dichloride |

-continued

| Structure | Nomenclature |
|---|---|
| 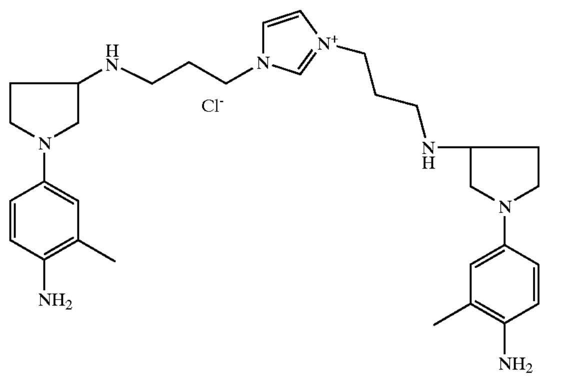 | 1,3-bis(3-{[1-(4-amino-3-methylphenyl)pyrrolidin-3-yl]amino}propyl)-1H-imidazol-3-ium chloride |
| 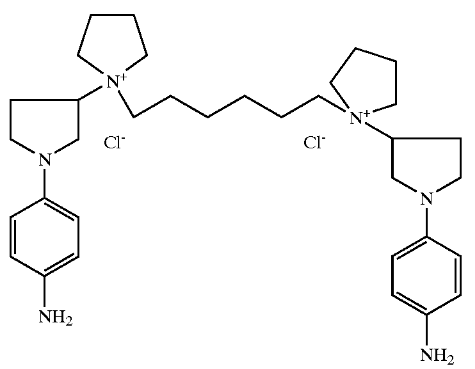 | N,N'-bis[1-(4-aminophenyl)pyrrolidin-3-yl]-N,N',dipyrrolidinehexane-1,6-diaminium dichloride |
| 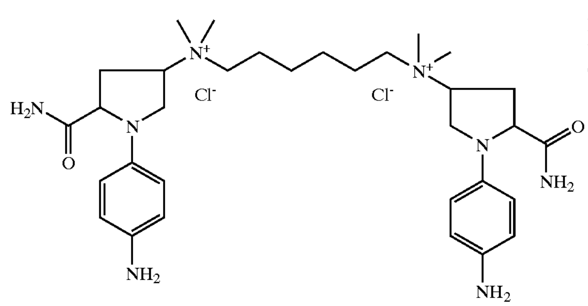 | N,N'-bis[1-(4-aminophenyl)pyrrolidin-5-amido-3-yl]-N,N,N',N'-tetramethylhexane-1,6-diaminium dichloride |
| 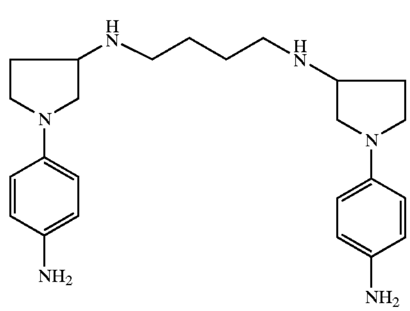 | N,N'-bis[1-(4-aminophenyl)pyrrolidin-3-yl]butane-1,2-diamine |

-continued

| Structure | Nomenclature |
|---|---|
| | N,N'-bis[1-(4-amino-3-méthylphenyl)pyrrolidin-3-yl]butane-1,2-diamine |
| 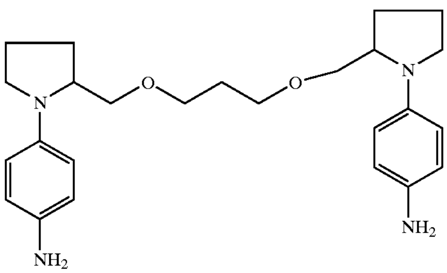 | 1,3-bis{[1-(4-aminophenyl)pyrrolidin-2-yl]methoxy}-propane |
| 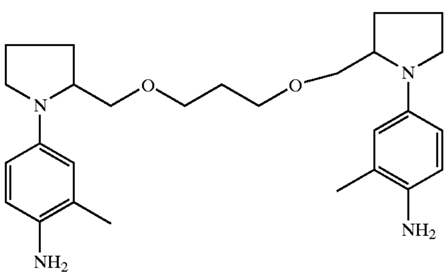 | 1,3-bis{[1-(4-amino-3-methylphenyl)pyrrolidin-2-yl]methoxy}-propane |
| 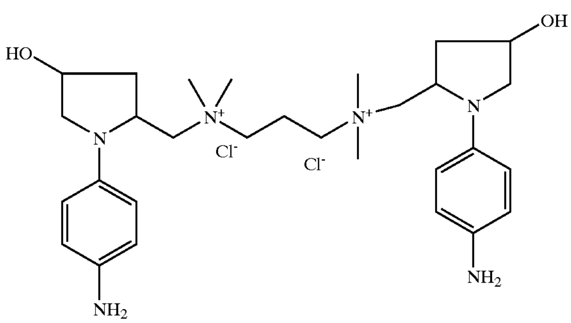 | N,N'-bis{[1-(4-aminophenyl)-4-hydroxypyrrolidin-2-yl]methyl}-N,N,N',N'-tetramethylpropane-1,3-diaminium dichloride |
| 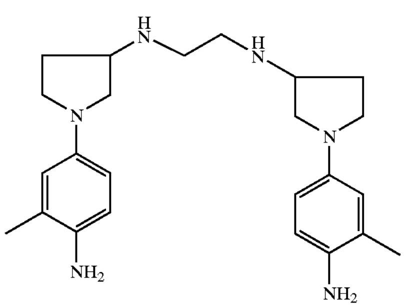 | N,N'-bis[1-(4-amino-3-methylphenyl)pyrrolidin-3-yl]ethane-1,2-diamine |

| Structure | Nomenclature |
|---|---|
| (structure shown) | N,N'-bis[1-(4-aminophenyl)pyrrolidin-3-yl]ethane-1,2-diamine |

For example, non-limiting mention may be made of the compounds of formula (I) chosen from:
N,N'-bis[1-(4-aminophenyl)pyrrolidin-3-yl]-N,N,N',N'-tetramethylhexane-1,6-diaminium dichloride
3-[1-(4-aminophenyl)pyrrolidin-3-yl]-1-(6-{1-[1-(4-aminophenyl)pyrrolidin-3-yl]-1H-imidazol-3-ium-3-yl}hexyl)-1H-imidazol-3-ium dichloride
1,3-bis[1-(4-aminophenyl)pyrrolidin-3-yl]-1H-imidazol-3-ium chloride
1,4-bis[1-(4-aminophenyl)pyrrolidin-3-yl]-1,4-dimethylpiperazinediium dichloride
1,4-bis[1-(4-aminophenyl)pyrrolidin-3-yl]-1,4-diazoniabicyclo[2.2.2]octane dichloride
N,N'-bis{[1-(4-aminophenyl)pyrrolidin-2-yl]methyl}-N,N,N',N'-tetramethylhexane-1,6-diaminium dichloride
3-{[1-(4-amino-3-methylphenyl)pyrrolidin-2-yl]methyl}-1-[6-(1-{[1-(4-amino-3-methylphenyl)pyrrolidin-2-yl]methyl}-1H-imidazol-3-ium-3-yl)hexyl]-1H-imidazol-3-ium dichloride
1,4-bis{[1-(4-aminophenyl)pyrrolidin-2-yl]methyl}-1,4-dimethylpiperazinediium dichloride
1,4-bis{[1-(4-aminophenyl)pyrrolidin-2-yl]methyl}-1,4-diazoniabicyclo[2.2.2]octane dichloride
N,N'-bis[1-(4-aminophenyl)pyrrolidin-3-yl]-N,N,N',N'-tetramethylpropane-1,3-diaminium dichloride
3-[1-(4-aminophenyl)pyrrolidin-3-yl]-1-(3-{1-[1-(4-aminophenyl)pyrrolidin-3-yl]-1H-imidazol-3-ium-3-yl}propyl)-1H-imidazol-3-ium dichloride
N,N'-bis{[1-(4-aminophenyl)pyrrolidin-2-yl]methyl}-N,N,N',N'-tetramethylpropane-1,3-diaminium dichloride
3-{[1-(4-aminophenyl)pyrrolidin-2-yl]methyl}-1-[3-(1-{[1-(4-aminophenyl)pyrrolidin-2-yl]methyl}-1H-imidazol-3-ium-3-yl)propyl]-1H-imidazol-3-ium dichloride
1,3-bis(3-{[1-(4-aminophenyl)pyrrolidin-3-yl]amino}propyl)-1H-imidazol-3-ium chloride
N,N'-bis[1-(4-aminophenyl)-5-(hydroxymethyl)pyrrolidin-3-yl]-N,N,N',N'-tetramethylhexane-1,6-diaminium dichloride
3-{[1-(4-aminophenyl)-4-hydroxypyrrolidin-2-yl]methyl}-1-[3-(1-{[1-(4-aminophenyl)-4-hydroxypyrrolidin-2-yl]methyl}-1H-imidazol-3-ium-3-yl)propyl]-1H-imidazol-3-ium dichloride
4-[1'-(4-aminophenyl)-2,2'-bipyrrolidin-1-yl]phenylamine
N,N'-bis[1-(4-aminophenyl)pyrrolidin-5-amido-3-yl]-N,N,N',N'-tetramethylhexane-1,6-diaminium dichloride
N,N'-bis[1-(4-aminophenyl)pyrrolidin-3-yl]butane-1,2-diamine
1,3-bis{[1-(4-aminophenyl)pyrrolidin-2-yl]methoxy}propane
N,N'-bis{[1-(4-aminophenyl)-4-hydroxypyrrolidin-2-yl]methyl}-N,N,N',N'-tetramethylpropane-1,3-diaminium dichloride
N,N'-bis[1-(4-aminophenyl)pyrrolidin-3-yl]ethane-1,2-diamine
N,N'-bis[1-(4-aminophenyl)pyrrolidin-3-yl]-N,N'-dipyrrolidinehexane-1,6-diaminium dichloride.

The dye composition of the present disclosure comprises, in a cosmetic medium that is suitable for dyeing keratin fibres, such as human hair, as the at least one oxidation base, a derivative of formula (I) as defined above.

The oxidation base(s) of the disclosure is (are) each generally present in an amount ranging approximately from 0.001% to 10%, by weight, relative to the total weight of the dye composition, and for example from 0.005% to 6%.

The dye composition of the disclosure may contain one or more couplers conventionally used for dyeing keratin fibres. Among these couplers, mention may be made of meta-phenylenediamines, meta-aminophenols, meta-diphenols, naphthalenic couplers and heterocyclic couplers, and the addition salts thereof.

Further examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the addition salts thereof with an acid.

In the composition of the present disclosure, the coupler (s) is (are) generally present in an amount ranging approximately from 0.001% to 10% by weight, relative to the total weight of the dye composition, for instance, from 0.005% to 6%.

The composition of the present disclosure may also comprise at least one additional oxidation base conventionally used in oxidation dyeing, other than those described above. By way of example, these additional oxidation bases may be chosen from para-phenylenediamines other than those described above, bis(phenyl)alkylenediamines, para-aminophenols, bis-para-aminophenols, ortho-aminophenols, heterocyclic bases, and the addition salts thereof.

Among the para-phenylenediamines which may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines, further mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols which can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned, for example, are 2-aminophenol, 2-amino-5-methylphenol, 2-amino-6-methylphenol and 5-acetamido-2-aminophenol, and the addition salts thereof with an acid.

Among the heterocyclic bases, mention may be made, for example, of pyridine derivatives, pyrimidine derivatives and pyrazole derivatives.

Among the pyridine derivatives which may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful according to the present disclosure are the 3-aminopyrazolo[1,5-a] pyridine oxidation bases or the addition salts thereof described, for example, in patent application FR 2 801 308. By way of example, mention may be made of pyrazolo[1, 5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo [1,5-a]pyrid-2-yl)methanol; 3,6-diaminopyrazolo[1,5-a] pyridine; 3,4-diaminopyrazolo[1,5-a]pyridine; pyrazolo[1, 5-a]pyridine-3,7-diamine; 7-morpholin-4-ylpyrazolo[1,5-a] pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino] ethanol; 2-[(3-aminopyrazolo[1,5-a]pyrid-7-yl)(2-hydroxyethyl)amino]ethanol; 3-aminopyrazolo-[1,5-a] pyrid-5-ol; 3-aminopyrazolo[1,5-a]pyrid-4-ol; 3-aminopyrazolo[1,5-a]pyrid-6-ol; 3-aminopyrazolo[1,5-a] pyrid-7-ol and also the addition salts thereof with an acid or with a base.

Among the pyrimidine derivatives which may be mentioned are the compounds described, for example, in patent DE 2 359 399 or patents JP 88-169 571; JP 05 63 124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo [1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a]pyrimidin-7-ylamino)ethanol, 2-(7-aminopyrazolo[1, 5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl) amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]-pyrimidine-3,7-diamine and 3-amino-5-methyl-7-imidazolylpropylamino-pyrazolo[1,5-a]pyrimidine, and the addition salts thereof with an acid and the tautomeric forms thereof, when a tautomeric equilibrium exists.

Among the pyrazole derivatives which may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3- hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) present in the composition of the invention is (are) each generally present in an amount ranging approximately from 0.001% to 10% by weight, relative to the total weight of the dye composition, for example from 0.005% to 6%.

In general, the addition salts of the oxidation bases and of the couplers that may be used in the context of the invention are chosen, for instance, from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines or alkanolamines.

The dye composition in accordance with the disclosure may also contain one or more direct dyes that may be chosen from, for example, nitrobenzene dyes, azo direct dyes and non-ionic direct dyes. These direct dyes may be of non-ionic, anionic or cationic nature.

The medium that is suitable for dyeing, also known as the dye support, generally comprises water or a mixture of water and at least one organic solvent to dissolve the compounds which would not be sufficiently soluble in water. As organic solvents, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

For example, the solvents may be present in an amount ranging approximately from 1% to 40% by weight, relative to the total weight of the dye composition, for instance from 5% to 30% by weight.

The dye composition in accordance with the disclosure can also contain various adjuvants conventionally used in compositions for dyeing the hair, such as anionic, cationic, non-ionic, amphoteric or zwitterionic surfactants or mixtures thereof, anionic, cationic, non-ionic, amphoteric or zwitterionic polymers or mixtures thereof, inorganic or organic thickeners, and, for example, anionic, cationic, non-ionic or amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each adjuvant ranging from 0.01% to 20% by weight, relative to the weight of the composition.

Needless to say, a person skilled in the art will take care to select this or these optional additional compounds such that the beneficial properties intrinsically associated with the oxidation dye composition in accordance with the disclosure are not, or are not substantially, adversely affected by the addition(s) envisaged.

The pH of the dye composition in accordance with the invention generally ranges from about 3 to 12, and for example, from 5 to 11. It may be adjusted to the desired value using acidifying or basifying agents usually used in the dyeing of keratin fibres, or alternatively using standard buffer systems.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

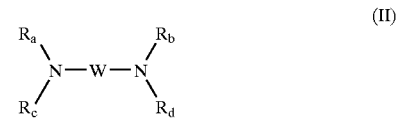

(II)

wherein: W is a propylene residue which is unsubstituted or substituted with a hydroxyl group or a $C_1$–$C_4$ alkyl radical; $R_a$, $R_b$, $R_c$ and $R_d$, which may be identical or different, are chosen from hydrogen atoms, $C_1$–$C_4$ alkyl radicals and $C_1$–$C_4$ hydroxyalkyl radicals.

The dye composition according to the present disclosure may be in various forms, such as in the form of liquids, creams or gels, or in any other form that is suitable for dyeing keratin fibres, for example human hair.

The process disclosed herein is a process wherein the composition according to the present disclosure as described above is applied to the fibres, in the presence of an oxidizing agent for a time that is sufficient to develop the desired colour. The colour may be developed at acidic, neutral or alkaline pH and the oxidizing agent may be added to the composition of the disclosure just at the time of use, or it may be used starting with an oxidizing composition containing it, which is applied simultaneously or sequentially to the composition of the disclosure.

According to one aspect of the disclosure, the composition is mixed, for instance, at the time of use, with a composition comprising, in a medium that is suitable for dyeing, at least one oxidizing agent, this oxidizing agent being present in an amount that is sufficient to develop a coloration. The mixture obtained is then applied to the keratin fibres. After an action time ranging from 3 to 50 minutes approximately, for example, 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases, and 4-electron oxygenases, for instance laccases. For example, mention may be made of hydrogen peroxide. The oxidizing agent may also be atmospheric oxygen.

The oxidizing composition may also comprise various adjuvants conventionally used in compositions for dyeing the hair and as defined above.

The pH of the oxidizing composition comprising the oxidizing agent is such that, after mixing with the dye composition, the pH of the resulting composition applied to the keratin fibres ranges for example, from 3 to 12 approximately such as, from 5 to 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels or any other form that is suitable for dyeing keratin fibres, for instance human hair.

Another aspect of the disclosure is a multi-compartment dyeing device or "kit", in which at least one compartment contains the dye composition as disclosed herein, and at least one other compartment contains an oxidizing composition. This device may be equipped with a means for applying the desired mixture to the hair, such as the devices described in patent FR-2 586 913 in the name of the Applicant.

Using this device, it is possible to dye keratin fibres using a process that includes mixing a dye composition comprising at least one oxidation base of formula (I) with an oxidizing agent, and applying the mixture obtained to the keratin fibres for a time that is sufficient to develop the desired coloration.

The examples that follow serve to illustrate the disclosure without, however, being limiting in nature.

EXAMPLES

Example 1

Synthesis of N,N'-bis[1-(4-aminophenyl)pyrrolidin-3-yl]-N,N'-trimethylhexane-1,6-diammonium chloride hydrochloride (3)

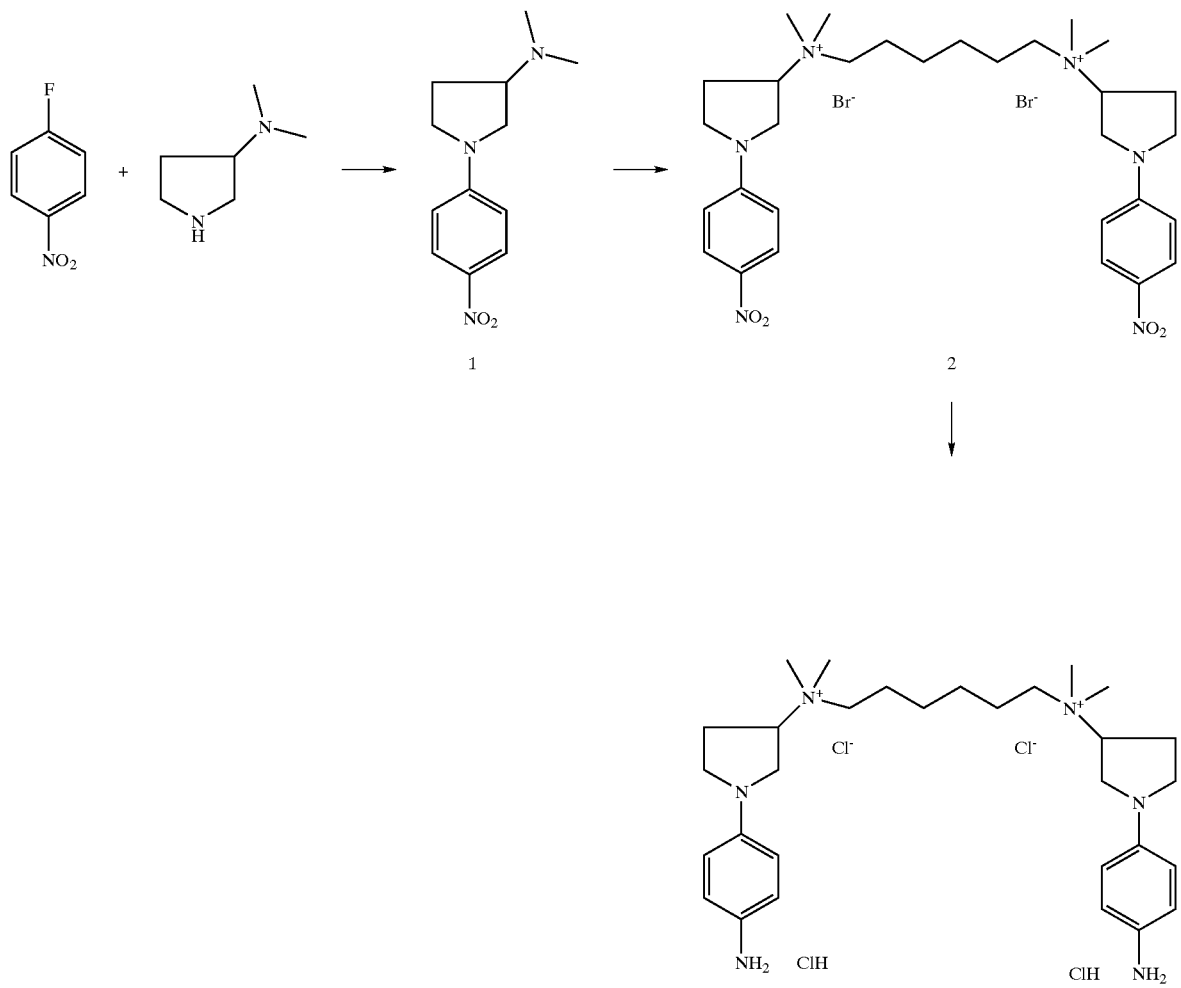

Synthesis of N,N'-bis[1-(4-nitrophenyl)pyrrolidin-3-yl]-N,N'-trimethylhexane-1,6-diammonium bromide (2)

0.513 g (0.00218 mol) of [1-(4-nitrophenyl)pyrrolidin-3-yl]dimethylamine and 0.244 g (0.001 mol) of dibromohexane were refluxed in 10 ml of methanol for six hours. After cooling to room temperature, the precipitate was washed with ethyl acetate and then filtered off. After draining by suction and drying the precipitate, 1.5 g of yellow powder (2) were obtained.

$^1$H NMR (400 MHz-DMSO) ppm 8.12 (d, 4H); 6.75 (d, 4H); 5.48 (m, 2H); 3.94 (m, 2H); 3.75 (m, 4H); 3.44 (m, 7H); 3.13 (s, 12H); 2.51–2.44 (m, 4H); 1.81 (m, 4H); 1.39 (m, 4H). Mass ESI+: m/z=277 [M2+/2]

Synthesis of N,N'-bis[1-(4-aminophenyl)pyrrolidin-3-yl]-N,N'-trimethylhexane-1,6-diammonium chloride (3)

1.5 g (0.0021 mol) of derivative (2) above dissolved in 250 ml of ethanol/water (50/50) were hydrogenated in the presence of palladium-on-charcoal under a hydrogen pressure of 10 bar, while heating to 65° C.; after filtering of the catalyst, the expected derivative (3) was isolated in the form of the hydrochloride. 1 g of white powder is obtained.

$^1$H NMR (400 MHz-D$_2$O) ppm: 7.20 (d, 2H); 6.72 (d, 2H); 4.31 (m, 2H); 3.70 (m, 2H); 3.55 (m, 4H); 3.33 (m, 4H); 3.21 (m, 2H); 3.03 (bs, 12H); 2.40 (m, 4H); 1.79 (m, 4H); 1.37 (m, 4H). Mass ESI+: m/z=247 [M2+/2]

Example 2

Synthesis of 3-[1-(4-aminophenyl)pyrrolidin-3-yl]-1-(3-{1-[1-(4-aminophenyl)pyrrolidin-3-yl]-1H-imidazol-3-ium-3-yl}propyl)-1H-imidazol-3-ium dibromide

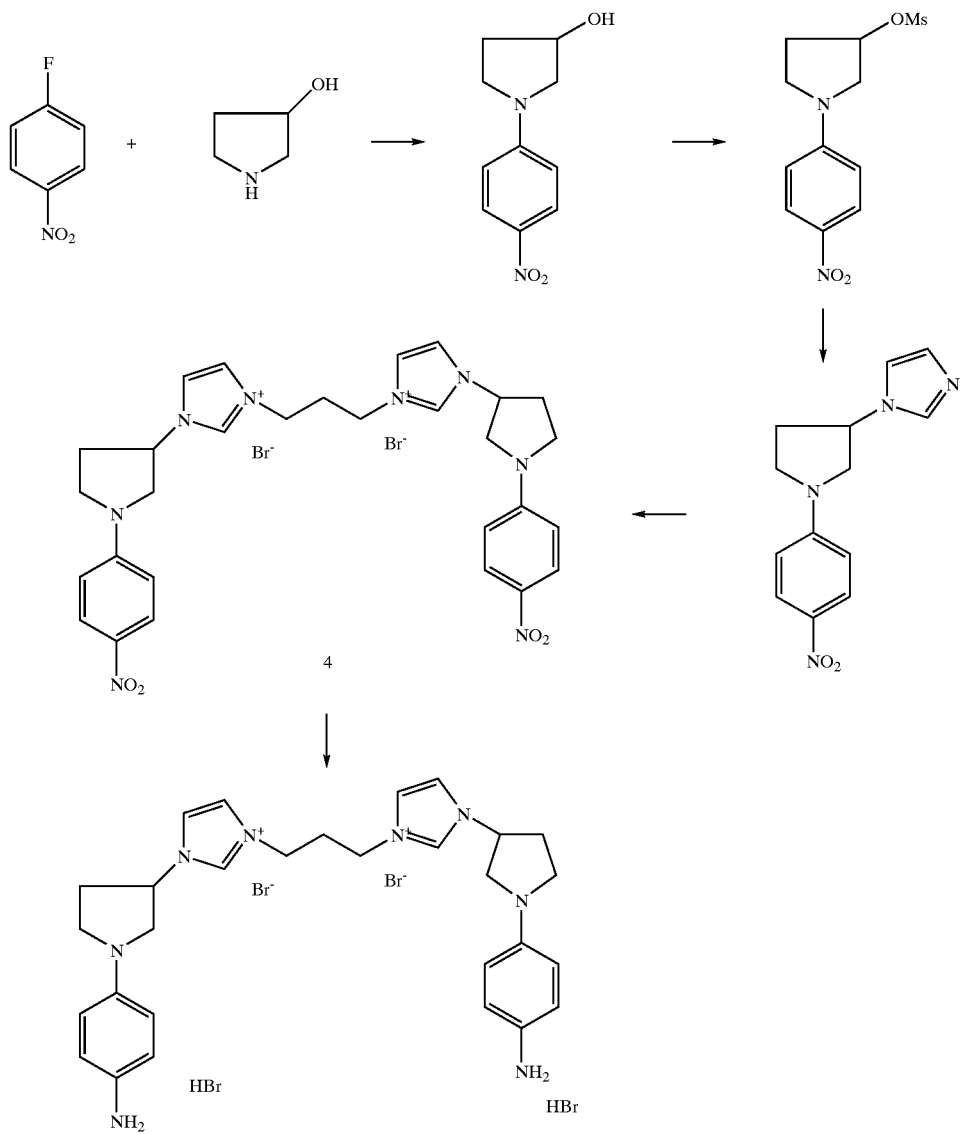

Synthesis of 3-[1-(4-nitrophenyl)pyrrolidin-3-yl]-1-
(3-{1-[1-(4-nitrophenyl)pyrrolidin-3-yl]-1H-
imidazol-3-ium-3-yl}propyl)-1H-imidazol-3-ium
dibromide (4)

3.5 g (0.0135 mol) of 1-[1-(4-nitrophenyl)pyrrolidin-3-yl]-1H-imidazole were heated to 100° C. in 12 ml of a pentanol/DMF mixture (50/50). 1 g (0.005 mol) of dibromopropane was added. The reaction medium was heated at 115° C. for 17 hours. The precipitate was filtered off while hot and washed with pentanol and then with ether. After draining by suction and drying the precipitate, 3.4 g of yellow powder (4) were obtained. 33% yield.

$^1$H NMR (400 MHz-DMSO) ppm: 9.41 (s, 2H); 8.13 (d, J=9 Hz, 4H); 7.93 (m, 2H); 7.88 (m, 2H); 6.71 (d, J=9 Hz, 4H); 5.30 (m, 2H); 4.25 (m, 4H); 3.98 (m, 2H); 3.83 (m, 2H); 3.70 (m, 2H); 3.60 (m, 2H); 2.46–2.40 (m, 6H). Mass ESI+: m/z=639 [$M^{2+}$+$Br^-$]$^+$, 557 [$M^{2+}$=$Br^-$–HBr]$^+$ Synthesis of 3-[1-(4-aminophenyl)pyrrolidin-3-yl]-
1-(3-{1-[1-(4-aminophenyl)pyrrolidin-3-yl]-1H-
imidazol-3-ium-3-yl}propyl)-1H-imidazol-3-ium
dibromide (5)

3.2 g (0.0044 mol) of derivative (4) above dissolved in a mixture of 60 ml of water/300 ml of ethanol were hydrogenated in the presence of palladium-on-charcoal under a hydrogen pressure of 9 bar and at 75° C. After filtering off the catalyst, the expected derivative (5) was isolated in the form of the hydrobromide. 3.4 g of white powder were obtained; 94% yield.

$^1$H NMR (400 MHz-DMSO) ppm: 8.84 (s, 2H); 7.41 (s, 2H); 7.41 (s, 2H); 7.17 (d, 4H); 6.69 (d, 4H); 5.14 (m, 2H); 4.22 (t, 4H); 3.69 (dd, 2H); 3.62 (dd, 2H); 3.55 (m, 2H); 3.34 (m, 2H); 2.59 (m, 2H); 2.42 (m, 2H); 2.3 (m, 2H). Mass ESI+: m/z=579 [$M^{2+}$+$Br^-$]$^+$, 249 [$M$]$^{2+}$/2

Example 3

Synthesis of 1,1'-bis(4-aminophenyl)[2,2']
bipyrrolidinyl-1-yl

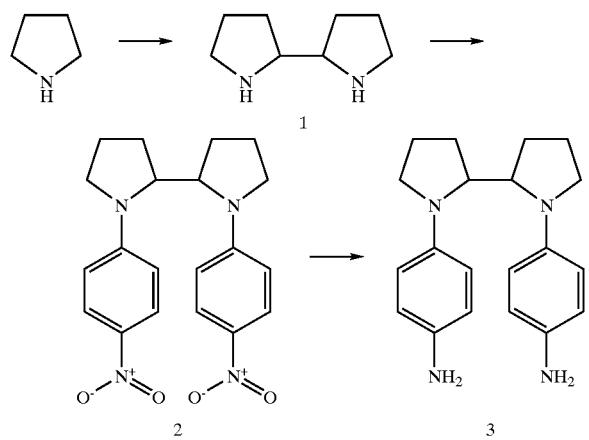

Preparation of [2,2']bipyrrolidinyl (1)

108 g (1.52 mol) of pyrrolidine and 11 g (0.076 mol) of di-t-butyl peroxide were heated in a stainless-steel autoclave at 140° C. for 9 hours. The reaction medium was evaporated to dryness and then treated with sodium borohydride in ethanol for 1 hour. After evaporating off the ethanol, the product was extracted with ethyl acetate and washed with water. On concentration, 2.6 g (80%) of a brown oil were obtained, which product was used without further modification for the rest of the synthesis.

Preparation of 1,1'-bis(4-nitrophenyl)[2,2']bipyrrolidinyl (2)

2.6 g (~15 mmol) of [2,2']bipyrrolidinyl (1) obtained above were refluxed in the presence of 5 g (35.7 mmol) of potassium carbonate and 5 g (35.7 mmol) of para-fluoronitrobenzene in 25 ml of water overnight. The agglomerate formed was filtered off and then rinsed with acetone and isopropanol to give 2.15 g of a mixture of two isomers (55/45) (44%). After purification by chromatography on silica gel, a majority isomer was isolated (1.2 g), the analyses for which were:

$^1$H NMR (400 MHz, DMSO): 1.92 (m, 2H, CH$_2$ 3'); 1.98 (m, 2H, CH$_2$ 4'); 2.11 (m, 2H, CH$_2$ 4'); 2.48 (m, 2H, CH$_2$ 3'); 3.14 (m, 2H, 1H, CH$_2$ 2'); 3.55 (m, 2H, CH$_2$ 2'); 4.13 (m, 2H, CH 5'); 6.39 (d, 4H, H2-H6); 7.81 (d, 4H, H3–H5). Mass ESI+: m/z=383 (M+H)$^+$ Preparation of 1,1'-bis(4-aminophenyl)[2,2']bipyrrolidinyl (3)

The derivative (2) was dissolved in 300 ml of ethanol and then hydrogenated in the presence of zinc. The expected derivative (3) was isolated in the form of the hydrochloride after acidifying the filtrate with hydrochloric acid.

Examples 1 to 4 of Dyeing in Alkylene Medium

| | Examples | | | |
|---|---|---|---|---|
| | 1 | 2 | 3 | 4 |
| N,N'-Bis[1-(4-aminophenyl)-pyrrolidin-3-yl]-N,N'-trimethylhexane-1,6-diammonium chloride hydrochloride (base) | 10$^{-3}$ mol | 10$^{-3}$ mol | 10$^{-3}$ mol | 10$^{-3}$ mol |
| 2-(2,4-Diaminophenoxy)ethanol dihydrochloride (coupler) | 10$^{-3}$ mol | — | — | — |
| 3-Amino-2-chloro-6-methylphenol hydrochloride (coupler) | — | 10$^{-3}$ mol | — | — |
| 3,6-Dimethyl-1H-pyrazolo[5,1-c][1,2,4]triazole (coupler) | — | — | 10$^{-3}$ mol | — |
| 2-Methyl-5-aminophenol (coupler) | — | — | — | 10$^{-3}$ mol |
| Dye support (1) | (*) | (*) | (*) | (*) |
| Demineralized water qs | 100 g | 100 g | 100 g | 100 g |

| | |
|---|---|
| 96° ethyl alcohol | 20.8 g |
| Sodium metabisulphite as an aqueous 35% solution | 0.23 g A.M. |
| Pentasodium salt of diethylenetriaminepentaacetic acid as an aqueous 40% solution | 0.48 g A.M. |
| C$_8$–C$_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 |

(*) Dye support (1) pH 9.5

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After leaving to act for 30 minutes, the locks were rinsed, washed with a standard shampoo, rinsed again and then dried.

The following dyeing results were obtained.

| | Examples | | | |
|---|---|---|---|---|
| | 1 | 2 | 3 | 4 |
| Shade observed | violet-blue | blue-violet | red-violet | violet |

Examples 5 to 7 of Dyeing in Acidic Medium

The dye compositions below were prepared:

| | Example | | |
|---|---|---|---|
| | 5 | 6 | 7 |
| N,N'-Bis[1-(4-aminophenyl)pyrrolidin-3-yl]-N,N'-trimethylhexane-1,6-diammonium chloride hydrochloride (base) | $10^{-3}$ mol | $10^{-3}$ mol | $10^{-3}$ mol |
| 2-(2,4-Diaminophenoxy)ethanol dihydrochloride (coupler) | $10^{-3}$ mol | — | — |
| 3-Amino-2-chloro-6-methylphenol hydrochloride (coupler) | — | $10^{-3}$ mol | — |
| 2-Methyl-5-aminophenol (coupler) | — | — | $10^{-3}$ mol |
| Dye support (2) | (*) | (*) | (*) |
| Demineralized water qs | 100 g | 100 g | 100 g |
| 96° ethyl alcohol | 20.8 g | | |
| Sodium metabisulphite as an aqueous 35% solution | 0.23 g A.M. | | |
| Pentasodium salt of diethylenetriaminepentaacetic acid as an aqueous 40% solution | 0.48 g A.M. | | |
| $C_8$–$C_{10}$ alkyl polyglucoside as an aqueous 60% solution | 3.6 g A.M. | | |
| Benzyl alcohol | 2.0 g | | |
| Polyethylene glycol containing 8 units of ethylene oxide | 3.0 g | | |
| $Na_2HPO_4$ | 0.28 g | | |
| $KH_2PO_4$ | 0.46 g | | |

(*) Dye support (2) pH 7

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After leaving to act for 30 minutes, the locks were rinsed, washed with a standard shampoo, rinsed again and then dried.

The following dyeing results were obtained.

| | Examples | | |
|---|---|---|---|
| | 5 | 6 | 7 |
| Shade observed | violet-blue | blue-violet | violet |

What is claimed is:

1. A compound chosen from bis-para-phenylenediamine derivatives substituted with at least one pyrrolidyl group, wherein said pyrrolidyl-substituted bis-para-phenylenediamine derivatives are chosen from derivatives corresponding to formula (I) and the corresponding salts thereof:

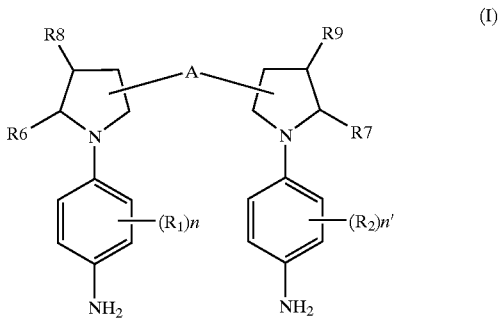

wherein:
n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms and $C_1$–$C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or a diazo, nitro, or nitroso radical, and wherein the chain may be substituted with at least one entity chosen from halogen atoms and hydroxyl, $C_1$–$C_6$ alkoxy, amino, mono-, di($C_1$–$C_6$)alkylamino and tri ($C_1$–$C_6$)alkylammonium radicals, and N—($C_1$–$C_6$) alkylimidazolinium radicals;

A is chosen from a covalent bond and linear and branched, saturated and unsaturated alkylene chains comprising from 1 to 14 carbon atoms, and wherein at least one of the carbon atoms of the chain may optionally be replaced with an entity chosen from: onium radical Z, oxygen, sulphur, silicon and nitrogen atoms, and CO, SO, and $SO_2$ groups, wherein the alkylene chains may optionally be substituted with at least one entity chosen from: halogen atoms, hydroxyl, $C_1$–$C_6$ alkoxy, amino, ($C_1$–$C_6$)alkylamino, and di($C_1$–$C_6$)alkylamino radicals;

$R_6$ and $R_7$, which may be identical or different, are chosen from: hydrogen atoms; carboxyl radicals; ($C_1$–$C_4$) alkylcarboxyl radicals; carbamoyl radicals; ($C_1$–$C_4$) (alkyl)carbamoyl radicals; (dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from carboxylic, ($C_1$–$C_6$)alkylcarbonyl, ($C_1$–$C_6$)alkoxycarbonyl, carbamoyl, mono- and di($C_1$–$C_6$)alkylcarbamoyl, tri($C_1$–$C_6$)alkylsilane, tri (($C_1$–$C_6$)alkyl)ammonium and N—($C_1$–$C_6$) alkylimidazolinium radicals;

$R_8$ and $R_9$, which may be identical or different, are chosen from: hydrogen atoms; hydroxyl radicals; ($C_1$–$C_4$)

alkyloxy radicals; amino radicals; mono- and di($C_1$–$C_4$)alkylamino radicals; thiol radicals; carboxyl radicals; ($C_1$–$C_4$)alkylcarboxyl radicals; carbamoyl radicals; ($C_1$–$C_4$)(alkyl and/or dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from: hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from: carboxylic, ($C_1$–$C_6$)alkylcarbonyl, ($C_1$–$C_6$)alkoxycarbonyl, carbamoyl, mono- and di($C_1$–$C_6$)alkylcarbamoyl, tri($C_1$–$C_6$)alkylsilane, tri (($C_1$–$C_6$)alkyl)ammonium, and N—($C_1$–$C_6$) alkylimidazolinium radicals.

2. The compound according to claim 1, wherein n and n', which may be identical or different, are equal to 0 or 1.

3. The compound according to claim 1, wherein $R_1$ and $R_2$, which may be identical or different, are chosen from a chlorine atom, a bromine atom, $C_1$–$C_4$ alkyl radicals, $C_1$–$C_4$ hydroxyalkyl radicals, $C_1$–$C_4$ aminoalkyl radicals, $C_1$–$C_4$ alkoxy radicals, $C_1$–$C_4$ hydroxyalkoxy radicals, tri($C_1$–$C_4$)alkylammonium($C_1$–$C_4$)alkyl radicals, and N—($C_1$–$C_4$)alkylimidazolinium($C_1$–$C_4$)alkyl radicals.

4. The compound according to claim 3, wherein $R_1$ and $R_2$, which may be identical or different, are chosen from methyl, isopropyl, tert-butyl, hydroxymethyl, 2-hydroxyethyl, 1,2-dihydroxyethyl, methoxy, isopropyloxy, 2-hydroxyethoxy, trimethylammoniummethyl, and N-methylimidazolinium radicals.

5. The compound according to claim 1, wherein A does not comprise a peroxide bond or a diazo, nitro or nitroso radical.

6. The compound according to claim 1, wherein A is chosen from a covalent bond and alkylene chains comprising from 1 to 8 carbon atoms.

7. The compound according to claim 1, wherein A is chosen from alkylene chains comprising from 1 to 8 carbon atoms, wherein at least one of the carbon atoms of the chain may optionally be replaced with an entity chosen from nitrogen and oxygen atoms.

8. The compound according to claim 1, wherein A is an alkylene chain comprising from 1 to 14 carbon atoms, and comprising at least one onium radical Z, wherein at least one carbon atom of the chain may optionally be replaced with an entity chosen from nitrogen and oxygen atoms.

9. The compound according to claim 1, wherein the onium radical Z corresponds to formula (II):

(II)

wherein:

$R_3$ and $R_4$, which may be identical or different, are chosen from $C_1$–$C_{15}$ alkyl radicals; $C_1$–$C_6$ monohydroxyalkyl radicals; $C_2$–$C_6$ polyhydroxyalkyl radicals; ($C_1$–$C_6$) alkoxy($C_1$–$C_6$)alkyl radicals; aryl radicals; benzyl radicals; amido($C_1$–$C_6$)alkyl radicals; tri($C_1$–$C_6$) alkylsilane($C_1$–$C_6$)alkyl radicals; $C_1$–$C_6$ aminoalkyl radicals; $C_1$–$C_6$ aminoalkyl radicals, wherein the amines are mono- and/or disubstituted with at least one entity chosen from $C_1$–$C_4$ alkyl, ($C_1$–$C_6$)alkylcarbonyl, amido, and ($C_1$–$C_6$)alkylsulphonyl radicals;

$R_3$ and $R_4$, together with the nitrogen atom to which they are attached, form a 5-, 6- or 7-membered heterocycle;

when at least two onium radicals of formula (II) are present in the chain A, at least one of the radicals $R_3$ and $R_4$ of one of the onium radicals may form a cyclic diammonium structure with at least one of the radicals $R_3$ and $R_4$ of the at least one other onium radical; and $Y^-$ is a counterion.

10. The compound according to claim 9, wherein $R_3$ and $R_4$, which may be identical or different, are chosen from $C_1$–$C_4$ alkyl radicals and $C_1$–$C_4$ hydroxyalkyl radicals.

11. The compound according to claim 9, wherein $R_3$ and $R_4$ together form a cationic ring chosen from pyrrolidinium, piperidinium, piperazinium and morpholinium rings, wherein the cationic ring may optionally be substituted with at least one entity chosen from halogen atoms, hydroxyl, $C_1$–$C_6$ alkyl, $C_1$–$C_6$ monohydroxyalkyl, $C_2$–$C_6$ polyhydroxyalkyl, $C_1$–$C_6$ alkoxy, tri($C_1$–$C_6$)alkylsilane ($C_1$–$C_6$)alkyl, amido, carboxyl, ($C_1$–$C_6$)alkyl, thio, $C_1$–$C_6$ thioalkyl, ($C_1$–$C_6$)alkylthio, amino, amino mono- or disubstituted with a ($C_1$–$C_6$)alkyl radical, ($C_1$–$C_6$)alkylcarbonyl, amido and ($C_1$–$C_6$)alkylsulphonyl radicals.

12. The compound according to claim 11, wherein $R_3$ and $R_4$ combined form a cationic ring chosen from pyrrolidinium, piperidinium and morpholinium rings.

13. The compound according to claim 1, wherein the onium radical Z is chosen from radicals of formula (III):

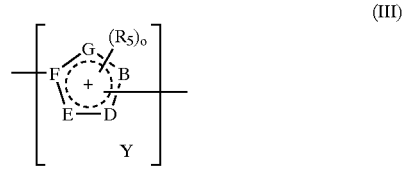

(III)

wherein:

the ring members B, D, E, F and G, which may be identical or different, are chosen from carbon, oxygen, sulphur and nitrogen atoms, such that B, D, E, F, and G are selected so as to form an aromatic ring cationized on the nitrogen, wherein the ring is chosen from pyrolium, pyrazolium, imidazolium, triazolium, oxazolium, isoxazolium, thiazolium and isothiazolium rings;

o is an integer ranging from 0 to 4;

$R_5$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$) alkylsilane($C_1$–$C_6$)alkyl radicals, ($C_1$–$C_6$)alkoxy ($C_1$–$C_6$)alkyl radicals, carbamyl($C_1$–$C_6$)alkyl radicals, ($C_1$–$C_6$)alkylcarboxy($C_1$–$C_6$)alkyl radicals and benzyl radicals; and when the at least one radical $R_5$ is attached to a carbon, $R_5$ may also be a radical chosen from hydroxyl, ($C_1$–$C_4$)alkyloxy, amino, ($C_1$–$C_4$)alkylamino and di($C_1$–$C_4$)alkylamino radicals, and $Y^-$ is a counterion.

14. The compound according to claim 13, wherein the cationic aromatic ring is chosen from imidazolium rings and thiazolium rings.

15. The compound according to claim 1, wherein the onium radical Z is chosen from radicals of formula (IV):

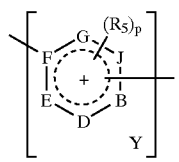

(IV)

wherein:

the ring members B, D, E, F, G and J, which may be identical or different, are chosen from carbon and nitrogen atoms, such that B, D, E, F, G, and J are selected so as to form an aromatic ring cationized on the nitrogen, wherein the ring is chosen from pyridinium, pyrimidinium, pyrazinium, triazinium and pyridazinium rings;

p is an integer ranging from 0 to 4;

$R_5$, which may be identical or different, is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, carbamyl($C_1$–$C_6$)alkyl radicals, ($C_1$–$C_6$)alkylcarboxy($C_1$–$C_6$)alkyl radicals, and benzyl radicals; and when the at least one radical $R_5$ is attached to a ring member chosen from carbon, $R_5$ may optionally be a radical chosen from hydroxyl, ($C_1$–$C_4$) alkyloxy, ($C_1$–$C_4$)alkylamino and di($C_1$–$C_4$) alkylamino radicals, and $Y^-$ is a counterion.

16. The compound according to claim 15, wherein the onium radical Z of formula (IV) is a cationized pyridinium ring.

17. The compound according to claim 13, wherein $R_5$ is a radical chosen from $C_1$–$C_4$ alkyl and $C_1$–$C_4$ hydroxyalkyl radicals.

18. The compound according to claim 15, wherein $R_5$ is a radical chosen from $C_1$–$C_4$ alkyl and $C_1$–$C_4$ hydroxyalkyl radicals.

19. The compound according to claim 1, wherein $R_6$ and $R_7$, which may be identical or different, are chosen from a hydrogen atom, $C_1$–$C_4$ hydroxyalkyl radicals, $C_1$–$C_4$ alkyl radicals, carboxyl radicals, carbamoyl radicals, mono- and di(($C_1$–$C_4$)alkyl)carbamoyl radicals, tri($C_1$–$C_4$) alkylammonium($C_1$–$C_4$)alkyl radicals, and N—($C_1$–$C_4$) alkylimidazolium($C_1$–$C_4$)alkyl radicals.

20. The compound according to claim 1, wherein $R_8$ and $R_9$, which may be identical or different, are chosen from hydrogen atoms, hydroxyl radicals, amino radicals, mono- and di($C_1$–$C_4$)alkylamino radicals, $C_1$–$C_4$ alkyl radicals, tri($C_1$–$C_4$)alkylammonium radicals, and N—($C_1$–$C_4$) alkylimidazolinium radicals.

21. A compound chosen from bis-para-phenylenediamine derivatives substituted with at least one pyrrolidyl group, wherein said pyrrolidyl-substituted bis-para-phenylenediamine derivatives are chosen from derivatives corresponding to formula (I') and the corresponding salts thereof:

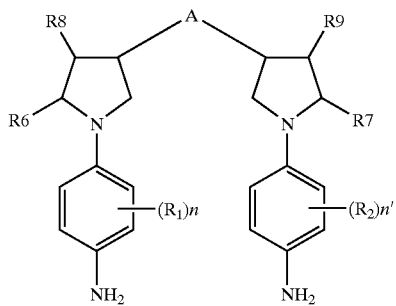

(I')

wherein:

n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms and $C_1$–$C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or a diazo, nitro, or nitroso radical, and wherein the chain may be substituted with at least one entity chosen from halogen atoms and hydroxyl, $C_1$–$C_6$ alkoxy, amino, mono-, di($C_1$–$C_6$)alkylamino, and tri ($C_1$–$C_6$)alkylammonium radicals, and N—($C_1$–$C_6$) alkylimidazolinium radicals;

A is chosen from a covalent bond and alkylene chains comprising from 1 to 14 carbon atoms, wherein the chains may be linear, branched, saturated or unsaturated, and wherein at least one of the carbon atoms of the chain may optionally be replaced with an entity chosen from: onium radical Z, oxygen, sulphur, silicon, and nitrogen atoms, and CO, SO, and $SO_2$ groups, wherein the alkylene chains may optionally be substituted with at least one entity chosen from: halogen atoms, hydroxyl, $C_1$–$C_6$ alkoxy, amino, ($C_1$–$C_6$) alkylamino, and di($C_1$–$C_6$)alkylamino radicals;

$R_6$ and $R_7$, which may be identical or different, are chosen from: hydrogen atoms; carboxyl radicals; ($C_1$–$C_4$) alkylcarboxyl radicals; carbamoyl radicals; ($C_1$–$C_4$) (alkyl)carbamoyl radicals; (dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated, and/or substituted with at least one radical chosen from carboxylic, ($C_1$–$C_6$)alkylcarbonyl, ($C_1$–$C_6$)alkoxycarbonyl, carbamoyl, mono- and di($C_1$–$C_6$)alkylcarbamoyl, tri($C_1$–$C_6$)alkylsilane, tri (($C_1$–$C_6$)alkyl)ammonium, and N—($C_1$–$C_6$) alkylimidazolinium radicals;

$R_8$ and $R_9$, which may be identical or different, are chosen from: hydrogen atoms; hydroxyl radicals; ($C_1$–$C_4$) alkyloxy radicals; amino radicals; mono- and di($C_1$–$C_4$)alkylamino radicals; thiol radicals; carboxyl radicals; ($C_1$–$C_4$)alkylcarboxyl radicals; carbamoyl radicals; ($C_1$–$C_4$)(alkyl and/or dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from: hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from: carboxylic, ($C_1$–$C_6$)alkylcarbonyl, ($C_1$–$C_6$)alkoxycarbonyl, carbamoyl, mono- and di($C_1$–$C_6$)alkylcarbamoyl, tri($C_1$–$C_6$)alkylsilane, tri (($C_1$–$C_6$)alkyl)ammonium, and N—($C_1$–$C_6$) alkylimidazolinium radicals.

22. The compound according to claim 21, wherein n and n', which may be identical or different, are equal to 0 or 1;

$R_1$ and $R_2$, which may be identical or different, are chosen from methyl, isopropyl, tert-butyl, hydroxymethyl, 2-hydroxyethyl, 1,2-dihydroxyethyl, methoxy, isopropoxy, 2-hydroxyethoxy, trimethylammoniummethyl, and N-methylimidazoliniummethyl radicals;

$R_6$ and $R_7$, which may be identical or different, are chosen from a hydrogen atom, $C_1$–$C_4$ hydroxyalkyl radicals, $C_1$–$C_4$ alkyl radicals, carboxyl radicals, carbamoyl radicals, mono- and di($C_1$–$C_4$)alkylcarbamoyl radicals, tri($C_1$–$C_4$)alkylammonium($C_1$–$C_4$)alkyl radicals, and N-alkyl($C_1$–$C_4$)imidazoliumalkyl radicals;

$R_8$ and $R_9$, which may be identical or different, are chosen from hydrogen atoms, hydroxyl radicals, amino radicals, mono- and di(($C_1$–$C_4$)alkyl)amino radicals, $C_1$–$C_4$ alkyl radicals, tri($C_1$–$C_4$)alkylammonium radicals, and N—($C_1$–$C_4$)alkylimidazolinium radicals;

A is a covalent bond or a radical chosen from:

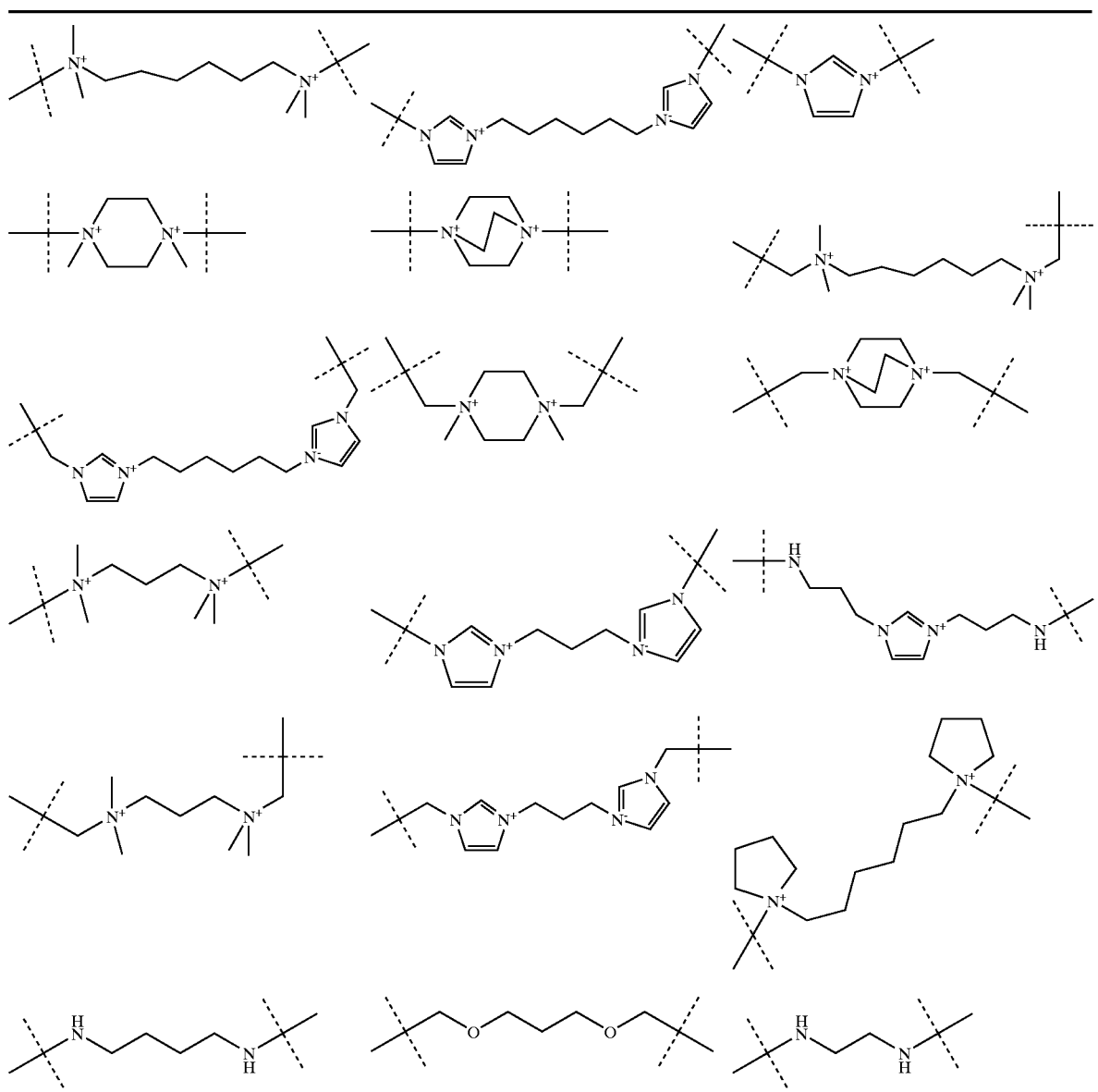

-continued

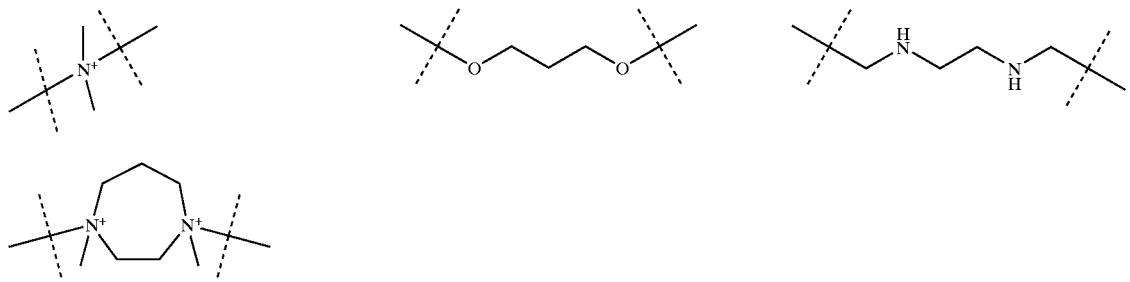

23. The compound according claim 1, chosen from
N,N'-bis[1-(4-aminophenyl)pyrrolidin-3-yl]-N,N,N',N'-tetramethylhexane-1,6-diaminium dichloride,
3-[1-(4-aminophenyl)pyrrolidin-3-yl]-1-(6-{1-[1-(4-aminophenyl)pyrrolidin-3-yl]-1H-imidazol-3-ium-3-yl}hexyl)-1H-imidazol-3-ium dichloride,
1,3-bis[1-(4-aminophenyl)pyrrolidin-3-yl]-1H-imidazol-3-ium chloride,
1,4-bis[1-(4-aminophenyl)pyrrolidin-3-yl]-1,4-dimethylpiperazinediium dichloride,
1,4-bis[1-(4-aminophenyl)pyrrolidin-3-yl]-1,4-diazoniabicyclo[2.2.2]octane dichloride,
N,N'-bis{[1-(4-aminophenyl)pyrrolidin-2-yl]methyl}-N,N,N',N'-tetramethylhexane-1,6-diaminium dichloride,
3-{[1-(4-amino-3-methylphenyl)pyrrolidin-2-yl]methyl}-1-[6-(1-{[1-(4-amino-3-methylphenyl)pyrrolidin-2-yl]methyl}-1H-imidazol-3-ium-3-yl)hexyl]-1H-imidazol-3-ium dichloride,
1,4-bis{[1-(4-aminophenyl)pyrrolidin-2-yl]methyl}-1,4-dimethylpiperazinediium dichloride,
1,4-bis{[1-(4-aminophenyl)pyrrolidin-2-yl]methyl}-1,4-diazoniabicyclo[2.2.2]octane dichloride,
N,N'-bis[1-(4-aminophenyl)pyrrolidin-3-yl]-N,N,N',N'-tetramethylpropane-1,3-diaminium dichloride,
3-[1-(4-aminophenyl)pyrrolidin-3-yl]-1-(3-{1-[1-(4-aminophenyl)pyrrolidin-3-yl]-1H-imidazol-3-ium-3-yl}propyl)-1H-imidazol-3-ium dichloride,
N,N'-bis{[1-(4-aminophenyl)pyrrolidin-2-yl]methyl}-N,N,N',N'-tetramethylpropane-1,3-diaminium dichloride,
3-{[1-(4-aminophenyl)pyrrolidin-2-yl]methyl}-1-[3-(1-{[1-(4-aminophenyl)pyrrolidin-2-yl]methyl}-1H-imidazol-3-ium-3-yl)propyl]-1H-imidazol-3-ium dichloride,
1,3-bis(3-{[1-(4-aminophenyl)pyrrolidin-3-yl]amino}propyl)-1H-imidazol-3-ium chloride,
N,N'-bis[1-(4-aminophenyl)-5-(hydroxymethyl)pyrrolidin-3-yl]-N,N,N',N'-tetramethylhexane-1,6-diaminium dichloride,
3-{[1-(4-aminophenyl)-4-hydroxypyrrolidin-2-yl]methyl}-1-[3-(1-{[1-(4-aminophenyl)-4-hydroxypyrrolidin-2-yl]methyl}-1H-imidazol-3-ium-3-yl)propyl]-1H-imidazol-3-ium dichloride,
4-[1'-(4-aminophenyl)-2,2'-bipyrrolidin-1-yl]phenylamine,
N,N'-bis[1-(4-aminophenyl)pyrrolidin-5-amido-3-yl]-N,N,N',N'-tetramethylhexane-1,6-diaminium dichloride,
N,N'-bis[1-(4-aminophenyl)pyrrolidin-3-yl]butane-1,2-diamine,
1,3-bis{[1-(4-aminophenyl)pyrrolidin-2-yl]methoxy}propane,
N,N'-bis{[1-(4-aminophenyl)-4-hydroxypyrrolidin-2-yl]methyl}-N,N,N',N'-tetramethylpropane-1,3-diaminium dichloride,
N,N'-bis[1-(4-aminophenyl)pyrrolidin-3-yl]ethane-1,2-diamine, and
N,N'-bis[1-(4-aminophenyl)pyrrolidin-3-yl]-N,N'-dipyrrolidinehexane-1,6-diaminium dichloride.

24. The compound according claim 23, chosen from
N,N'-bis[1-(4-aminophenyl)pyrrolidin-3-yl]-N,N,N',N'-tetramethylhexane-1,6-diaminium dichloride,
3-[1-(4-aminophenyl)pyrrolidin-3-yl]-1-(6-{1-[1-(4-aminophenyl)pyrrolidin-3-yl]-1H-imidazol-3-ium-3-yl}hexyl)-1H-imidazol-3-ium dichloride,
1,3-bis[1-(4-aminophenyl)pyrrolidin-3-yl]-1H-imidazol-3-ium chloride,
1,4-bis[1-(4-aminophenyl)pyrrolidin-3-yl]-1,4-dimethylpiperazinediium dichloride,
1,4-bis[1-(4-aminophenyl)pyrrolidin-3-yl]-1,4-diazoniabicyclo[2.2.2]octane dichloride,
N,N'-bis{[1-(4-aminophenyl)pyrrolidin-2-yl]methyl}-N,N,N',N'-tetramethylhexane-1,6-diaminium dichloride,
3-{[1-(4-amino-3-methylphenyl)pyrrolidin-2-yl]methyl}-1-[6-(1-{[1-(4-amino-3-methylphenyl)pyrrolidin-2-yl]methyl}-1H-imidazol-3-ium-3-yl)hexyl]-1H-imidazol-3-ium dichloride,
1,4-bis{[1-(4-aminophenyl)pyrrolidin-2-yl]methyl}-1,4-dimethylpiperazinediium dichloride,
1,4-bis{[1-(4-aminophenyl)pyrrolidin-2-yl]methyl}-1,4-diazoniabicyclo[2.2.2]octane dichloride,
N,N'-bis[1-(4-aminophenyl)pyrrolidin-3-yl]-N,N,N',N'-tetramethylpropane-1,3-diaminium dichloride,
3-[1-(4-aminophenyl)pyrrolidin-3-yl]-1-(3-{1-[1-(4-aminophenyl)pyrrolidin-3-yl]-1H-imidazol-3-ium-3-yl}propyl)-1H-imidazol-3-ium dichloride,
N,N'-bis{[1-(4-aminophenyl)pyrrolidin-2-yl]methyl}-N,N,N',N'-tetramethylpropane-1,3-diaminium dichloride,
3-{[1-(4-aminophenyl)pyrrolidin-2-yl]methyl}-1-[3-(1-{[1-(4-aminophenyl)pyrrolidin-2-yl]methyl}-1H-imidazol-3-ium-3-yl)propyl]-1H-imidazol-3-ium dichloride,
1,3-bis(3-{[1-(4-aminophenyl)pyrrolidin-3-yl]amino}propyl)-1H-imidazol-3-ium chloride,
N,N'-bis[1-(4-aminophenyl)-5-(hydroxymethyl)pyrrolidin-3-yl]-N,N,N',N'-tetramethylhexane-1,6-diaminium dichloride,
3-{[1-(4-aminophenyl)-4-hydroxypyrrolidin-2-yl]methyl}-1-[3-(1-{[1-(4-aminophenyl)-4- hydroxypyrrolidin-2-yl]methyl}-1H-imidazol-3-ium-3-yl)propyl]-1H-imidazol-3-ium dichloride, 4-[1'-(4-aminophenyl)-2,2'-bipyrrolidin-1-yl]phenylamine, N,N'-bis[1-(4-aminophenyl)pyrrolidin-5-amido-3-yl]-N,N,N',N'-tetramethylhexane-1,6-diaminium dichloride, N,N'-bis[1-(4-aminophenyl)pyrrolidin-3-yl]butane-1,2-diamine, 1,3-bis{[1-(4-aminophenyl)pyrrolidin-2-yl]methoxy}propane, N,N'-bis{[1-(4-aminophenyl)-4-hydroxypyrrolidin-2-yl]methyl}-N,N,N',N'-tetramethylpropane-1,3-diaminium dichloride, N,N'-bis[1-(4-aminophenyl)pyrrolidin-3-yl]ethane-1,2-diamine, and N,N'-bis[1-(4-aminophenyl)pyrrolidin-3-yl]-N,N'-dipyrrolidinehexane-1,6-diaminium dichloride.

25. A dye composition comprising at least one oxidation base comprising at least one pyrrolidyl-substituded bis-para-phenylenediamine derivative chosen from derivatives of formula (I) and the corresponding salts thereof:

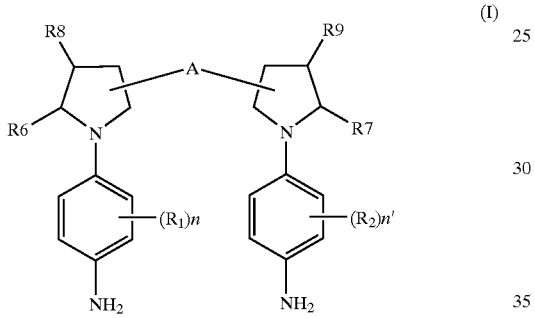

(I)

wherein:
n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms and $C_1$–$C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or a diazo, nitro, or nitroso radical, and wherein the chain may be substituted with at least one entity chosen from halogen atoms and hydroxyl, $C_1$–$C_6$ alkoxy, amino, mono-, di($C_1$–$C_6$)alkylamino, and tri ($C_1$–$C_6$)alkylammonium radicals, and N—($C_1$–$C_6$) alkylimidazolinium radicals;

A is chosen from a covalent bond and alkylene chains comprising from 1 to 14 carbon atoms, wherein the chains may be linear, branched, saturated or unsaturated, and wherein at least one of the carbon atoms of the chain may optionally be replaced with an entity chosen from: onium radical Z, oxygen, sulphur, silicon and nitrogen atoms, and CO, SO, and $SO_2$ groups, wherein the alkylene chains may optionally be substituted with at least one entity chosen from: halogen atoms, hydroxyl, $C_1$–$C_6$ alkoxy, amino, ($C_1$–$C_6$) alkylamino, and di($C_1$–$C_6$)alkylamino radicals;

$R_6$ and $R_7$, which may be identical or different, are chosen from: hydrogen atoms; carboxyl radicals; ($C_1$–$C_4$) alkylcarboxyl radicals; carbamoyl radicals; ($C_1$–$C_4$) (alkyl)carbamoyl radicals; (dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from carboxylic, ($C_1$–$C_6$)alkylcarbonyl, ($C_1$–$C_6$)alkoxycarbonyl, carbamoyl, mono- or di($C_1$–$C_6$)alkylcarbamoyl, tri($C_1$–$C_6$)alkylsilane, tri (($C_1$–$C_6$)alkyl)ammonium and N—($C_1$–$C_6$) alkylimidazolinium radicals;

$R_8$ and $R_9$, which may be identical or different, are chosen from: hydrogen atoms; hydroxyl radicals; ($C_1$–$C_4$) alkyloxy radicals; amino radicals; mono- and di($C_1$–$C_4$)alkylamino radicals; thiol radicals; carboxyl radicals; ($C_1$–$C_4$)alkylcarboxyl radicals; carbamoyl radicals; ($C_1$–$C_4$)(alkyl and/or dialkyl)carbamoyl radicals; tri($C_1$–$C_6$)alkylsilane radicals; tri(($C_1$–$C_6$)alkyl) ammonium radicals; N—($C_1$–$C_6$)alkylimidazolinium radicals; $C_1$–$C_{15}$ alkyl radicals; $C_1$–$C_{15}$ alkyl radicals which may optionally be unsaturated and/or substituted with at least one entity chosen from: hydroxyl, ($C_1$–$C_6$) alkyloxy, amino, mono- and di($C_1$–$C_6$)alkylamino, thiol, and ($C_1$–$C_6$)alkylsulphonic radicals, and halogen atoms; $C_1$–$C_{15}$ alkyl radicals which may optionally be unsaturated and/or substituted with at least one radical chosen from: carboxylic, ($C_1$–$C_6$)alkylcarbonyl, ($C_1$–$C_6$)alkoxycarbonyl, carbamoyl, mono- and/or di($C_1$–$C_6$)alkylcarbamoyl, tri($C_1$–$C_6$)alkylsilane, tri (($C_1$–$C_6$)alkyl)ammonium, and N—($C_1$–$C_6$) alkylimidazolinium radicals.

26. The composition according to claim 25, further comprising at least one coupler chosen from meta-phenylenediamines, meta-aminophenols, meta-diphenols, naphthalene-based couplers, heterocyclic couplers, and the addition salts thereof.

27. The composition according to claim 25, further comprising at least one additional oxidation base other than the at least one oxidation base of formula (I), chosen from para-phenylenediamines, bis(phenyl)alkylenediamines, para-aminophenols, ortho-aminophenols, heterocyclic bases, and the addition salts thereof.

28. The composition according to claim 25, wherein the at least one oxidation base comprising a derivative of formula (I) is present in the composition in an amount ranging approximately from 0.001% to 10% by weight, relative to the total weight of the dye composition.

29. The composition according to claim 27, wherein the at least one additional oxidation base that does not comprise a derivative of formula (I) is present in the composition in an amount ranging approximately from 0.001% to 10% by weight, relative to the total weight of the dye composition.

30. The composition according to claim 26, wherein the at least one coupler is present in an amount ranging approximately from 0.001% to 10% by weight, relative to the total weight of the dye composition.

31. The composition according to claim 25, further comprising a cosmetic medium that is suitable for dyeing keratin fibres.

32. A process for the oxidation dyeing of keratin fibres, comprising applying to the fibres, in the presence of at least one oxidizing agent, for a time that is sufficient to develop the desired coloration,
a dye composition comprising at least one oxidation base comprising at least one pyrrolidyl-substituded bis-para-phenylenediamine derivative chosen from derivatives of formula (I) and the corresponding salts thereof:

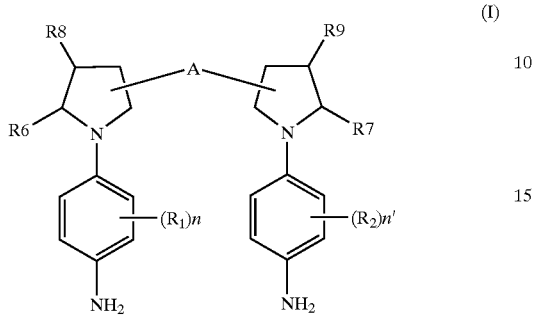

wherein:
n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms and $C_1-C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or a diazo, nitro, or nitroso radical, and wherein the chain may be substituted with at least one entity chosen from halogen atoms and hydroxyl, $C_1-C_6$ alkoxy, amino, mono-, di($C_1-C_6$)alkylamino, tri($C_1-C_6$)alkylammonium radicals, and N—($C_1-C_6$) alkylimidazolinium radicals;

A is chosen from a covalent bond, and alkylene chains comprising from 1 to 14 carbon atoms, wherein the chains may be linear, branched, saturated or unsaturated, and wherein at least one of the carbon atoms of the chain may optionally be replaced with an entity chosen from: onium radical Z, oxygen, sulphur, silicon and nitrogen atoms, and CO, SO, and $SO_2$ groups, wherein the alkylene chains may optionally be substituted with at least one entity chosen from: halogen atoms, hydroxyl, $C_1-C_6$ alkoxy, amino, ($C_1-C_6$) alkylamino, and di($C_1-C_6$)alkylamino radicals;

$R_6$ and $R_7$, which may be identical or different, are chosen from: hydrogen atoms; carboxyl radicals; ($C_1-C_4$) alkylcarboxyl radicals; carbamoyl radicals; ($C_1-C_4$) (alkyl)carbamoyl radicals; (dialkyl)carbamoyl radicals; tri($C_1-C_6$)alkylsilane radicals; tri(($C_1-C_6$)alkyl) ammonium radicals; N—($C_1-C_6$)alkylimidazolinium radicals; $C_1-C_{15}$ alkyl radicals; $C_1-C_{15}$ alkyl radicals which may optionally be unsaturated and/or substituted with at least one entity chosen from hydroxyl, ($C_1-C_6$) alkyloxy, amino, mono- and di($C_1-C_6$)alkylamino, thiol, and ($C_1-C_6$)alkylsulphonic radicals, and halogen atoms; $C_1-C_{15}$ alkyl radicals which may optionally be unsaturated and/or substituted with at least one radical chosen from: carboxylic, ($C_1-C_6$)alkylcarbonyl, ($C_1-C_6$)alkoxycarbonyl, carbamoyl, mono- and/or di($C_1-C_6$)alkylcarbamoyl, tri($C_1-C_6$)alkylsilane, tri (($C_1-C_6$)alkyl)ammonium, and N—($C_1-C_6$) alkylimidazolinium radicals;

$R_8$ and $R_9$, which may be identical or different, are chosen from: hydrogen atoms; hydroxyl radicals; ($C_1-C_4$) alkyloxy radicals; amino radicals; mono- and di($C_1-C_4$)alkylamino radicals; thiol radicals; carboxyl radicals; ($C_1-C_4$)alkylcarboxyl radicals; carbamoyl radicals; ($C_1-C_4$)(alkyl and/or dialkyl)carbamoyl radicals; tri($C_1-C_6$)alkylsilane radicals; tri(($C_1-C_6$)alkyl) ammonium radicals; N—($C_1-C_6$)alkylimidazolinium radicals; $C_1-C_{15}$ alkyl radicals; $C_1-C_{15}$ alkyl radicals which may optionally be unsaturated and/or substituted with at least one entity chosen from: hydroxyl, ($C_1-C_6$) alkyloxy, amino, mono- and/or di($C_1-C_6$)alkylamino, thiol, and ($C_1-C_6$)alkylsulphonic radicals, and halogen atoms; $C_1-C_{15}$ alkyl radicals which may optionally be unsaturated and/or substituted with at least one radical chosen from: carboxylic, ($C_1-C_6$)alkylcarbonyl, ($C_1-C_6$)alkoxycarbonyl, carbamoyl, mono- and/or di($C_1-C_6$)alkylcarbamoyl, tri($C_1-C_6$)alkylsilane, tri (($C_1-C_6$)alkyl)ammonium, and N—($C_1-C_6$) alkylimidazolinium radicals.

33. The process according to claim 32, wherein the at least one oxidizing agent is chosen from hydrogen peroxide, urea peroxide, alkali metal bromates, persalts, peracids, and oxidase enzymes.

34. A multi-compartment kit or device for the oxidation dyeing of keratin fibers, wherein at least one compartment comprises a dye composition comprising at least one oxidation base comprising at least one pyrrolidyl-substituted bis-para-phenylenediamine derivative chosen from derivatives of formula (I) and the corresponding salts thereof:

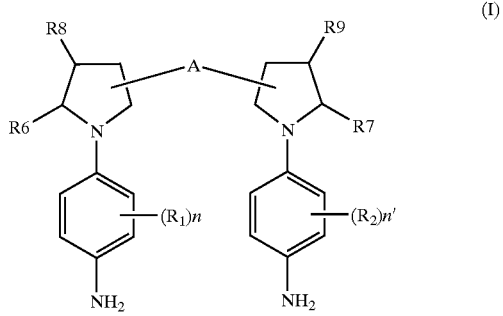

wherein:
n and n', which may be identical or different, are integers ranging from 0 to 4, wherein if either n or n' is greater than or equal to 2, then $R_1$ and $R_2$ may be identical or different;

$R_1$ and $R_2$, which may be identical or different, are each chosen from halogen atoms and $C_1-C_6$ hydrocarbon-based chains which may be aliphatic, alicyclic, saturated or unsaturated, wherein at least one of the carbon atoms of the chain may optionally be replaced with at least one entity chosen from oxygen, nitrogen, silicon, and sulphur atoms, SO groups, and $SO_2$ groups, with the proviso that $R_1$ and $R_2$ do not comprise a peroxide bond or a diazo, nitro, or nitroso radical, and wherein the chain may be substituted with at least one entity chosen from halogen atoms and hydroxyl, $C_1-C_6$ alkoxy, amino, mono-, di($C_1-C_6$)alkylamino radicals, tri($C_1-C_6$)alkylammonium radicals, and N—($C_1-C_6$) alkylimidazolinium radicals;

A is chosen from a covalent bond, and alkylene chains comprising from 1 to 14 carbon atoms, wherein the chains may be linear, branched, saturated or unsaturated, and wherein at least one of the carbon atoms of the chain may optionally be replaced with an entity chosen from: onium radical Z, oxygen, sulphur, silicon and nitrogen atoms, and CO, SO, and $SO_2$ groups, wherein the alkylene chains may optionally be substituted with at least one entity chosen from: halogen atoms, hydroxyl, $C_1$–$C_6$ alkoxy, amino, $(C_1$–$C_6)$ alkylamino, and di$(C_1$–$C_6)$alkylamino radicals;

$R_6$ and $R_7$, which may be identical or different, are chosen from: hydrogen atoms; carboxyl radicals; $(C_1$–$C_4)$ alkylcarboxyl radicals; carbamoyl radicals; $(C_1$–$C_4)$ (alkyl)carbamoyl radicals; (dialkyl)carbamoyl radicals; tri$(C_1$–$C_6)$alkylsilane radicals; tri$((C_1$–$C_6)$alkyl) ammonium radicals; N—$(C_1$–$C_6)$alkylimidazolinium radicals; $C_1$–$C_{15}$ alkyl radicals; $C_1$–$C_{15}$ alkyl radicals which may optionally be unsaturated and/or substituted with at least one entity chosen from hydroxyl, $(C_1$–$C_6)$ alkyloxy, amino, mono- and di$(C_1$–$C_6)$alkylamino, thiol, and $(C_1$–$C_6)$alkylsulphonic radicals, and halogen atoms; $C_1$–$C_{15}$ alkyl radicals which may optionally be unsaturated and/or substituted with at least one radical chosen from carboxylic, $(C_1$–$C_6)$alkylcarbonyl, $(C_1$–$C_6)$alkoxycarbonyl, carbamoyl, mono- or di$(C_1$–$C_6)$alkylcarbamoyl, tri$(C_1$–$C_6)$alkylsilane, tri$((C_1$–$C_6)$alkyl)ammonium, and N—$(C_1$–$C_6)$ alkylimidazolinium radicals;

$R_8$ and $R_9$, which may be identical or different, are chosen from: hydrogen atoms; hydroxyl radicals; $(C_1$–$C_4)$ alkyloxy radicals; amino radicals; mono- and di$(C_1$–$C_4)$alkylamino radicals; thiol radicals; carboxyl radicals; $(C_1$–$C_4)$alkylcarboxyl radicals; carbamoyl radicals; $(C_1$–$C_4)$(alkyl and/or dialkyl)carbamoyl radicals; tri$(C_1$–$C_6)$alkylsilane radicals; tri$((C_1$–$C_6)$alkyl) ammonium radicals; N—$(C_1$–$C_6)$alkylimidazolinium radicals; $C_1$–$C_{15}$ alkyl radicals; $C_1$–$C_{15}$ alkyl radicals which may optionally be unsaturated and/or substituted with at least one entity chosen from: hydroxyl, $(C_1$–$C_6)$ alkyloxy, amino, mono- and di$(C_1$–$C_6)$alkylamino, thiol, and $(C_1$–$C_6)$alkylsulphonic radicals, and halogen atoms; $C_1$–$C_{15}$ alkyl radicals which may optionally be unsaturated and/or substituted with at least one radical chosen from: carboxylic, $(C_1$–$C_6)$alkylcarbonyl, $(C_1$–$C_6)$alkoxycarbonyl, carbamoyl, mono- and/or di$(C_1$–$C_6)$alkylcarbamoyl, tri$(C_1$–$C_6)$alkylsilane, tri$((C_1$–$C_6)$alkyl)ammonium, and N—$(C_1$–$C_6)$ alkylimidazolinium radicals, and at least one compartment comprising at least one oxidizing agent.

* * * * *

UNITED STATES PATENT AND TRADEMARK OFFICE
CERTIFICATE OF CORRECTION

PATENT NO. : 6,923,835 B2
DATED : August 2, 2005
INVENTOR(S) : Stéphane Sabelle et al.

It is certified that error appears in the above-identified patent and that said Letters Patent is hereby corrected as shown below:

Column 39,
Line 67, "pyrrolidyl-substituded" should read -- pyrrolidyl-substituted --.

Column 43,
Line 64, "pyrrolidyl-substituded" should read -- pyrrolidyl-substituted --.

Columns 45-46,
In the first row of structures, " 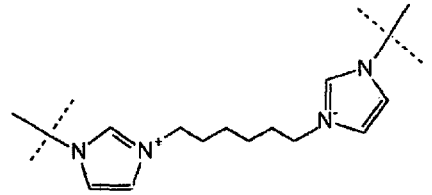 " should read

-- 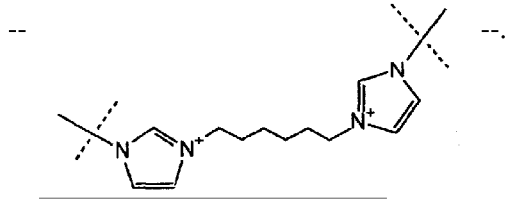 --.

In the third row of structures, " 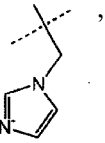 " should read

-- 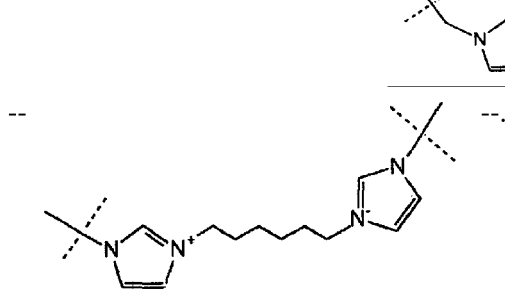 --.

In the fourth row of structures, " 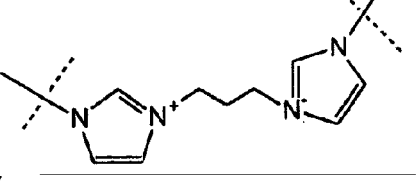 " should read

-- 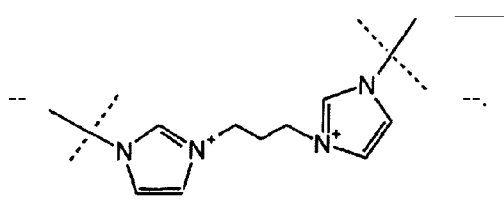 --.

UNITED STATES PATENT AND TRADEMARK OFFICE
CERTIFICATE OF CORRECTION

PATENT NO. : 6,923,835 B2
DATED : August 2, 2005
INVENTOR(S) : Stéphane Sabelle et al.

It is certified that error appears in the above-identified patent and that said Letters Patent is hereby corrected as shown below:

Columns 45-46 (cont'd),
In the fifth row of structures, " 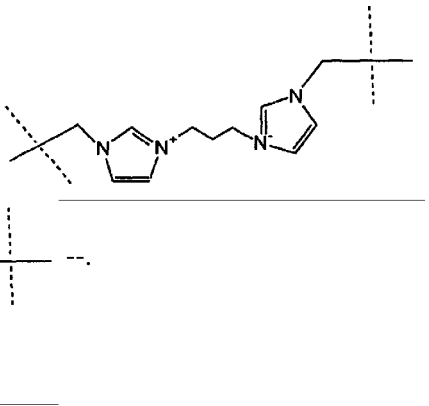 " should read -- --.

Column 47,
Line 17, "according claim" should read -- according to claim --.

Column 48,
Line 27, "according claim" should read -- according to claim --.

Column 49,
Line 20, "pyrrolidyl-substituded" should read -- pyrrolidyl-substituted --.

Column 51,
Line 4, "pyrrolidyl-substituded" should read -- pyrrolidyl-substituted --.

Signed and Sealed this

Fifteenth Day of November, 2005

JON W. DUDAS
*Director of the United States Patent and Trademark Office*